US010376398B2

(12) United States Patent
Ondersma et al.

(10) Patent No.: US 10,376,398 B2
(45) Date of Patent: Aug. 13, 2019

(54) PROSTHESIS DELIVERY DEVICE WITH A PUSHER EXTENSION AND AN EXTENSION DILATOR

(71) Applicant: COOK MEDICAL TECHNOLOGIES LLC, Bloomington, IN (US)

(72) Inventors: Joel Ondersma, Bloomington, IN (US); Blayne A. Roeder, Bloomington, IN (US); Edwin E. Macatangay, Bloomington, IN (US); Siddharth Vad, Irvine, CA (US); Davorin K. Skender, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 582 days.

(21) Appl. No.: 15/044,558

(22) Filed: Feb. 16, 2016

(65) Prior Publication Data
US 2016/0262919 A1 Sep. 15, 2016

Related U.S. Application Data

(60) Provisional application No. 62/132,641, filed on Mar. 13, 2015.

(51) Int. Cl.
A61F 2/954 (2013.01)
A61F 2/966 (2013.01)
(Continued)

(52) U.S. Cl.
CPC .............. A61F 2/966 (2013.01); A61F 2/844 (2013.01); A61F 2/856 (2013.01); A61F 2/95 (2013.01);
(Continued)

(58) Field of Classification Search
CPC ........ A61F 2/0795; A61F 2/954; A61F 2/966; A61F 2230/013; A61F 2/844;
(Continued)

(56) References Cited

U.S. PATENT DOCUMENTS 5,713,948 A * 2/1998 Uflacker ................... A61F 2/07
606/194
2003/0078593 A1* 4/2003 Bates .................. A61B 17/221
606/127

(Continued)

FOREIGN PATENT DOCUMENTS

EP 2777606 A1 9/2014

OTHER PUBLICATIONS

European Search Report for corresponding EP 16275035 dated Jul. 18, 2016, 5 pages.

Primary Examiner — Ryan J. Severson
Assistant Examiner — Christian D Knauss
(74) Attorney, Agent, or Firm — Brinks Gilson & Lione

(57) ABSTRACT

A delivery device and methods for deploying an endovascular prosthesis within the common and internal iliac arteries are described. The device comprises a pusher catheter having a proximal end and a pusher extension extending proximally therefrom. A tubular prosthesis having a side branch is releasably coupled to the pusher extension. An extension dilator extends proximally from the proximal end of the pusher catheter, extends at least partially along an external surface of the main tubular body, into a distal end of the side branch and exits a proximal end of the tubular prosthesis. The extension dilator can be tracked over a guide wire which serves to both position the device within a vessel and also to facilitate cannulation of an internal iliac artery.

19 Claims, 16 Drawing Sheets

(51) Int. Cl.
    *A61F 2/844*     (2013.01)
    *A61F 2/856*     (2013.01)
    *A61F 2/95*     (2013.01)
    *A61F 2/07*     (2013.01)
    *A61F 2/06*     (2013.01)

(52) U.S. Cl.
    CPC ............... *A61F 2/954* (2013.01); *A61F 2/07* (2013.01); *A61F 2002/065* (2013.01); *A61F 2002/9505* (2013.01); *A61F 2230/0069* (2013.01)

(58) Field of Classification Search
    CPC ............... A61F 2/856; A51F 2002/065; A51F 2002/9505; A51F 2002/9511; A51F 2002/9522; A51F 2002/9665
    See application file for complete search history.

(56) References Cited

U.S. PATENT DOCUMENTS

| | | | |
|---|---|---|---|
| 2004/0143316 A1* | 7/2004 | Spiridigliozzi | A61B 17/12022 623/1.13 |
| 2007/0219614 A1* | 9/2007 | Hartley | A61F 2/07 623/1.11 |
| 2009/0270971 A1* | 10/2009 | Xiao | A61F 2/07 623/1.14 |
| 2011/0270376 A1 | 11/2011 | Hartley | |
| 2014/0194970 A1* | 7/2014 | Chobotov | A61F 2/954 623/1.12 |

\* cited by examiner

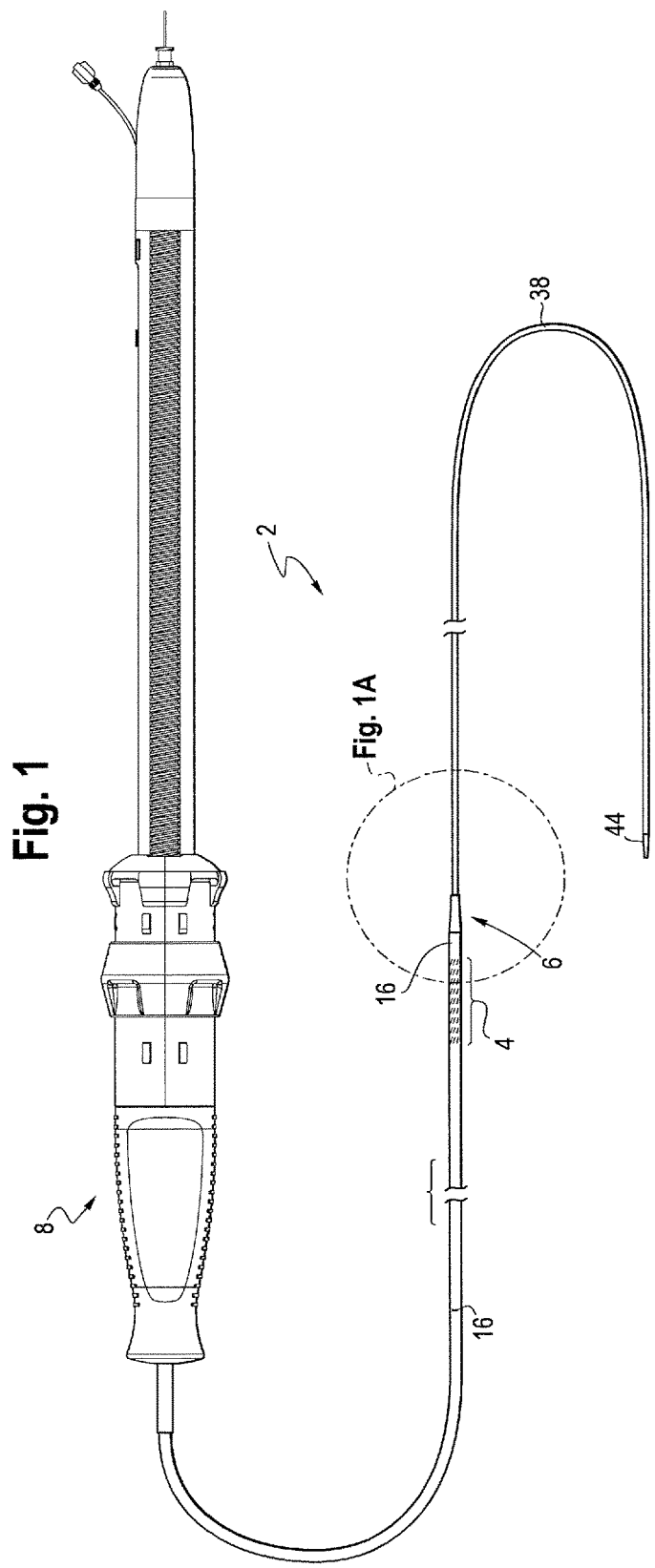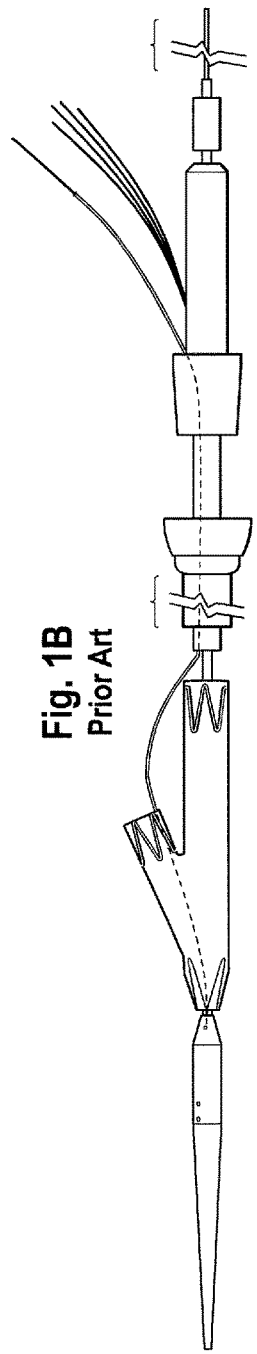

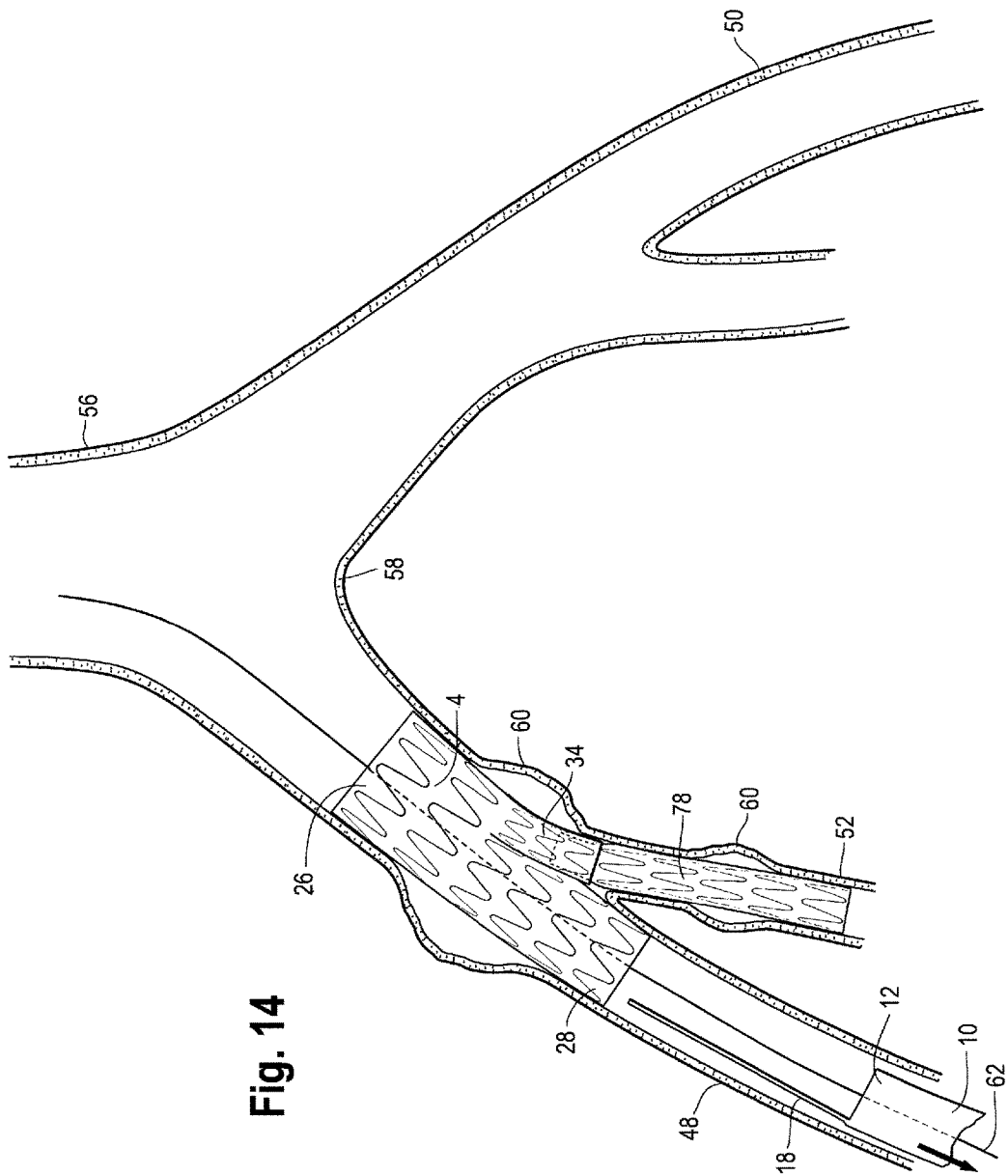

PROSTHESIS DELIVERY DEVICE WITH A PUSHER EXTENSION AND AN EXTENSION DILATOR

RELATED APPLICATIONS

This application claims priority to U.S. Provisional application Ser. No. 62/132,641 filed on Mar. 13, 2015, which is incorporated by reference herein in its entirety.

BACKGROUND

This invention relates generally to medical devices and methods of using the same, and more particularly, to an endovascular prosthesis delivery device and methods for placement and deployment of the graft in the lumen of a branched vessel such as an iliac artery.

An endovascular prosthesis, such as a stent graft, may be inserted into an anatomical vessel or duct for various purposes. For example, stent grafts are used for treatment of vasculature in the human or animal body to bypass a repair or defect in the vasculature or to maintain or restore patency in a formerly blocked or constricted passageway. For example, a stent graft may extend proximally and/or distally away from a vascular defect, including a diseased portion of an aneurysm, and engage a healthy portion of a vessel wall. In many cases, however, such a damaged or defective portion of the vasculature may include a branched or side vessel such as a common iliac artery and/or an internal iliac artery extending from the common iliac artery. Commonly, to repair a defect in these branched vessels, a stent graft is provided which, when deployed in the common iliac artery, has a side branch or arm positioned towards the opening to the internal iliac artery and then, if desired, another stent graft can be deployed through the side branch into the internal iliac artery to bypass a diseased portion thereof and restore the blood flow path to the internal iliac artery.

Generally, when deploying an endovascular stent graft into a vessel lumen, it is possible to obtain access to such a lumen from one or both ends of the vessel where necessary, thereby facilitating placement of a graft in the desired portion of the lumen. However, the internal iliac artery, which extends from the common iliac artery below the aortic bifurcation, is a blind vessel because there is no practical way of performing a minimally invasive endovascular procedure into that vessel other than by entry from the common iliac artery.

Access to and introduction of a stent graft into the common and/or internal iliac arteries and successful deployment of a stent graft in such vessels may often depend upon a favorable layout of the arteries and, in many cases, access is difficult. Accordingly, a prosthesis delivery device having a pusher catheter with an extension for releasably attaching to the prosthesis, as well as an extension dilator which may facilitate both cannulating the internal iliac artery as well as tracking the device into position within a vessel with a single guide wire is described.

While this invention will be generally discussed in relation to a delivery device for a stent graft and method of deployment thereof into a common iliac artery where it is necessary to extend a side branch from a main portion or body of the graft into an internal iliac artery, it is also contemplated that the invention is not so limited and may relate to any body or vessel lumen in which such a deployment is necessary or desired.

SUMMARY

The present disclosure provides a prosthesis delivery device and methods for delivering and deploying a prosthesis into one or more vessels. In one example, a prosthesis delivery device is disclosed. The delivery device comprises a pusher catheter having a proximal end, a distal end and a lumen extending therebetween. A pusher extension extends proximally from the proximal end of the pusher catheter and a tubular prosthesis is releasably coupled to the pusher extension. The tubular prosthesis comprises a main tubular body having a proximal end and a distal end and a tubular side arm extending from the main tubular body, with the distal end of the tubular prosthesis being adjacent to the proximal end of the pusher catheter. The pusher extension is external to the tubular prosthesis and extends along an external surface of the tubular prosthesis. An extension dilator having a first end and a second end and a lumen extending between the first and second ends extends proximally from the proximal end of the pusher catheter, at least partially along the external surface of the main tubular body, into a distal end of the tubular side arm and exits a proximal end of the tubular prosthesis.

In another example, a prosthesis delivery device is disclosed. The prosthesis delivery device comprises a pusher catheter having a proximal end and a pusher extension extending proximally from the proximal end of the pusher catheter. A tubular prosthesis is releasably coupled to the pusher extension, wherein the tubular prosthesis comprises a main tubular body having a proximal end and a distal end and a lumen extending therebetween, wherein the distal end of the tubular prosthesis is adjacent to the proximal end of the pusher catheter. The pusher extension extends along an external surface of the tubular prosthesis on one side of the prosthesis. An extension dilator extends proximally from the proximal end of the pusher catheter, through at least a portion of the lumen of the main tubular body, and exits a proximal end of the tubular prosthesis. The extension dilator has a radially outwardly flared portion and the proximal end of the sheath tapers radially inwardly and wherein the proximal tapered end of the sheath frictionally engages the extension dilator at a location adjacent the radially outwardly flared portion.

A method for treating a diseased vessel is disclosed. In one example, the method comprises providing a prosthesis delivery device comprising a pusher catheter having a proximal end and a pusher extension extending proximally from the proximal end of the pusher catheter. A tubular prosthesis is releasably coupled to the pusher extension, wherein the tubular prosthesis comprises a main tubular body having a proximal end and a distal end and a tubular side arm extending from the main tubular body and wherein the distal end of the tubular prosthesis is adjacent to the proximal end of the pusher catheter. The pusher extension is external to the tubular prosthesis and extends along an external surface of the tubular prosthesis. The extension dilator has a lumen and extends proximally from the proximal end of the pusher catheter, extending at least partially along an external surface of the main tubular body, into a distal end of the tubular side arm and exits a proximal end of the tubular prosthesis. A delivery sheath has a first position in which a proximal end of the sheath frictionally engages the extension dilator at a location proximal to the proximal end of the prosthesis and a second distally retracted position. The method further comprises tracking the delivery device over a guide wire within a patient's vasculature to position the prosthesis in a main vessel with the tubular side arm adjacent an opening to a branch vessel, wherein the guide wire extends through the lumen of the extension dilator and retracting the sheath to move it from the first position to the second position to expose at least the proximal end of the stent graft and the tubular side arm. The method further comprises withdrawing the extension dilator from the vasculature through the proximal end of the prosthesis leaving the guide wire in place to facilitate cannulation of a branch vessel, tracking an auxiliary sheath over the guide wire into the proximal end of the prosthesis and through the lumen of the tubular side arm until a proximal end of the auxiliary sheath is located adjacent the opening of the branch vessel to facilitate cannulation of the branch vessel, delivering an extension prosthesis through the auxiliary sheath into the branch vessel, and deploying the tubular prosthesis and the extension prosthesis and removing the delivery device from the patient's vasculature.

BRIEF DESCRIPTION OF THE DRAWINGS

FIG. 1 illustrates one example of a delivery device in a delivery configuration for introducing a stent graft into a patient's vasculature.

FIG. 1B illustrates one example of a prior art pre-loaded delivery device comprising a stent graft releasably coupled to an inner cannula and a nose cone located at the proximal end of the inner cannula.

FIGS. 4-14 illustrate a portion of a patient's vasculature and an example of the various stages of the introduction, placement and deployment of a stent graft into a common iliac artery and an internal iliac artery.

DETAILED DESCRIPTION

Throughout this specification, the terms "distal" and "distally" are used for a position or direction closest to the physician performing a procedure and the terms "proximal" and "proximally" are used for a position or direction away from the physician. The term "ipsilateral" is used to indicate that the diseased vessel(s) being accessed during a given procedure are on the same side of the body (right or left) as the vascular access device/introducer, while "contralateral" signifies that the vessel(s) of interest are on the opposite side of the body.

The embodiments described below are in connection with systems and methods for the introduction and deployment of an implantable medical device in a vessel, such as endovascular prosthesis, but could also be used for deploying a range of implantable medical devices including, but not limited to, stents, stent grafts, occlusion devices and the like.

Referring first to FIG. 1B, a prior art stent graft delivery device is shown. The prior art delivery device includes a stent graft releasably secured to an inner catheter and a nose cone extending proximally from the proximal end of the inner catheter. In a pre-deployment configuration, a sheath (not shown) preferably extends coaxially over the stent graft and up to at least a distal end of the nose cone to hold the stent graft in radially-inwardly contracted delivery configuration. This prior art device is described in further detail in U.S. Pub. No. 2011/0270376 to Hartley entitled "Introducer For A Side Branch Device" which is incorporated by reference herein in its entirety.

Figure 1A:
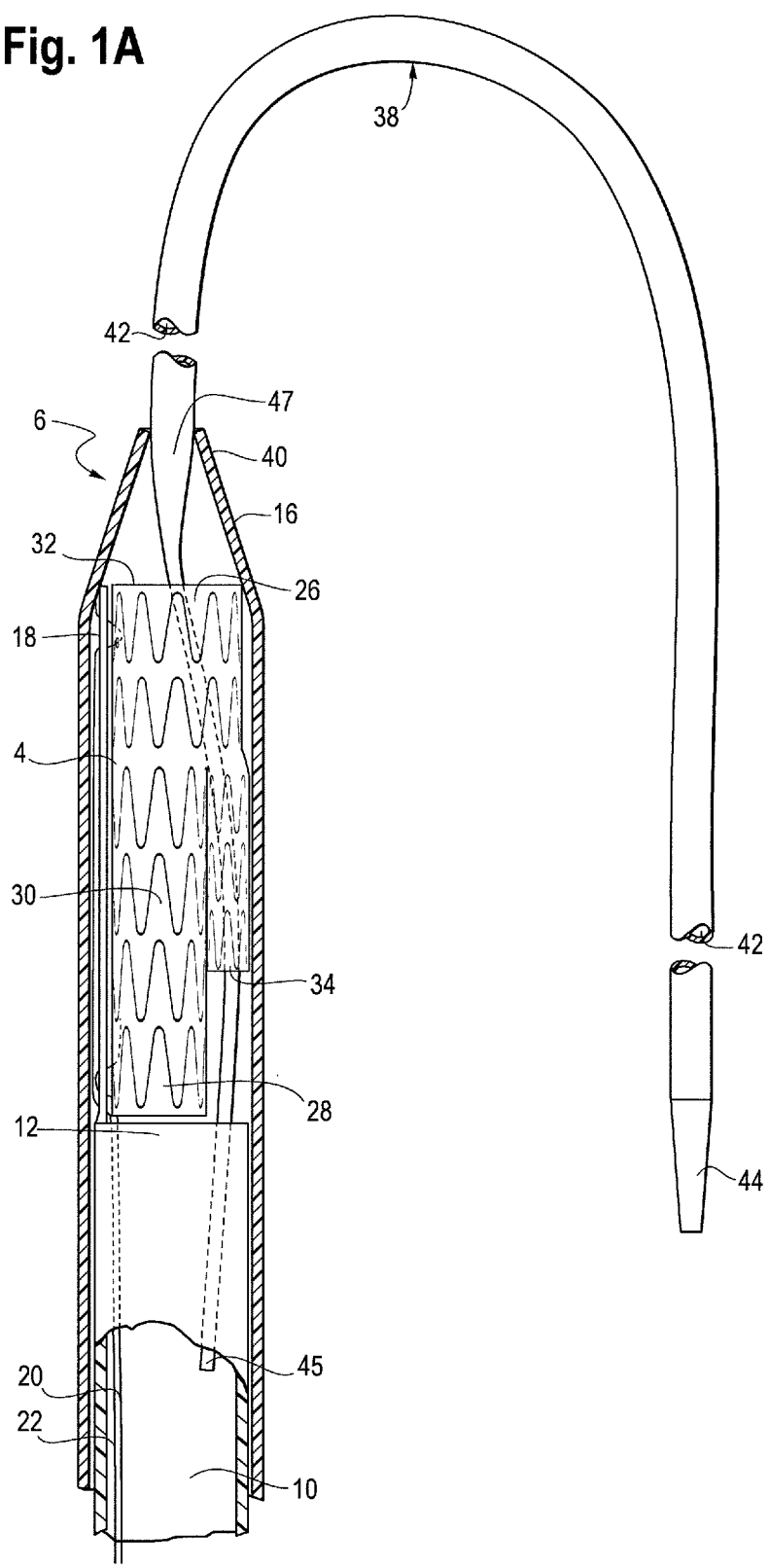
FIG. 1A illustrates an enlarged portion of FIG. 1 showing detail of an extension dilator extending proximally from the proximal end of a sheath.

Referring now to FIG. 1, one example of a stent graft delivery device of the present invention is shown generally at 2. As shown in FIG. 1A, a stent graft 4 is releasably secured to the proximal end 6 of the delivery device. During a medical procedure to position and deploy the stent graft 4, the proximal end 6 of the device 2 will travel through the vessel lumen to a desired deployment site. The distal external manipulation or handle section 8 which may include a handle portion, which is acted upon by a user to manipulate the device 2, remains outside of the patient throughout the procedure. The delivery device 2 is preferably "pre-loaded", or in other words, before the delivery device is introduced into the patient's vasculature, it is pre-assembled with mechanisms that facilitate graft delivery and deployment already arranged thereon. The delivery and deployment mechanisms may include, for example, one or more guide wires, catheters, sheaths, stent grafts and combinations thereof, which are arranged on and/or are carried by the device 2 and which remain in place during delivery of the stent graft 4 into a patient's vasculature. In one non-limiting example, the delivery device 2 may include one or more mechanisms that aid in the placement and deployment of a stent graft 4 in the common iliac artery and/or one or more mechanisms that aid in the placement and deployment of an additional or side branch extension stent graft 78 in an internal iliac artery in accordance with the systems and methods described herein.

Figure 2:
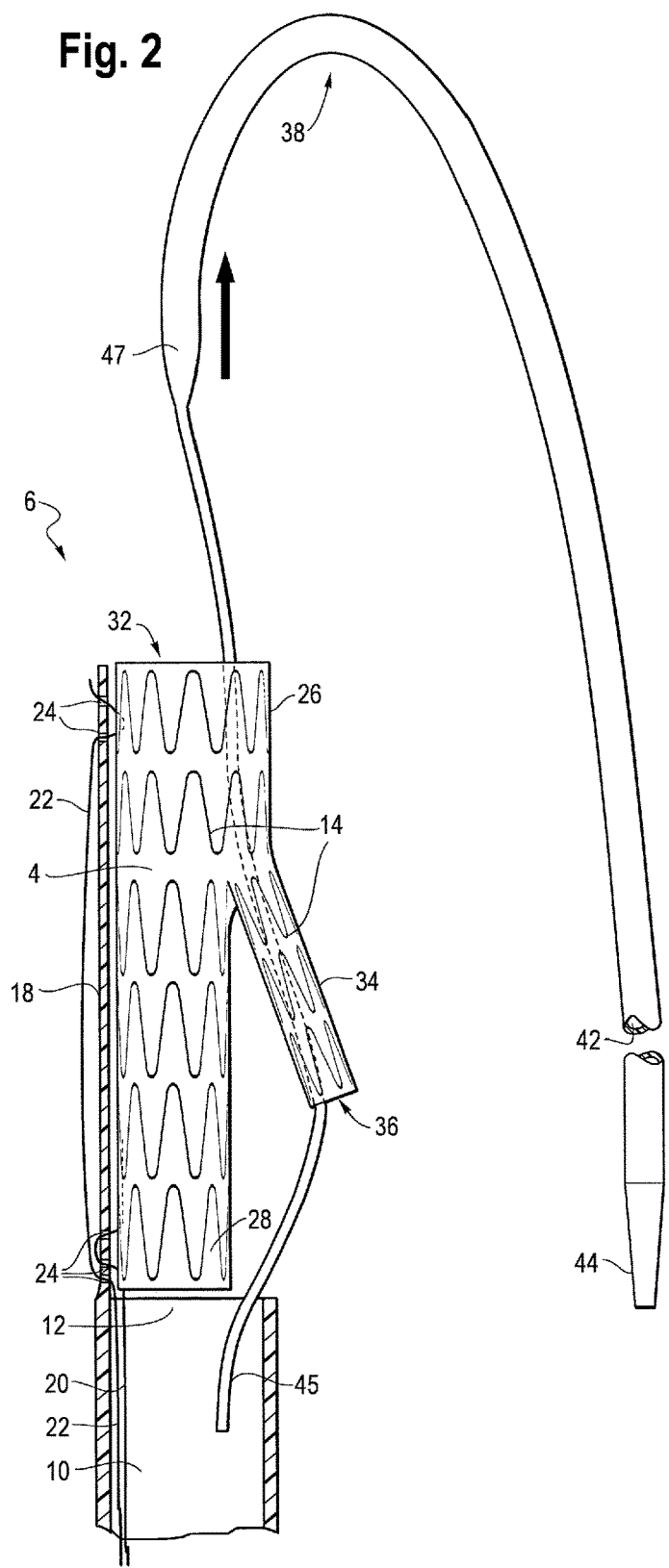
FIG. 2 shows one example of the proximal end of a delivery device with a pusher extension releasably secured to the proximal and distal ends of a stent graft and an extension dilator extending proximally from the proximal end of the stent graft.
Figure 2A:
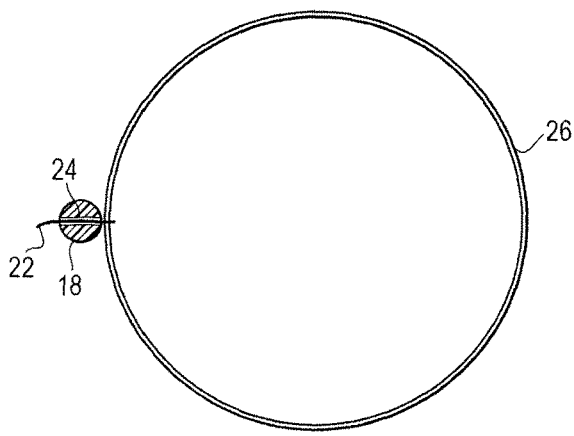
FIG. 2A illustrates a cross-sectional view of one embodiment of a pusher extension shown in FIG. 2.
Figure 2B:
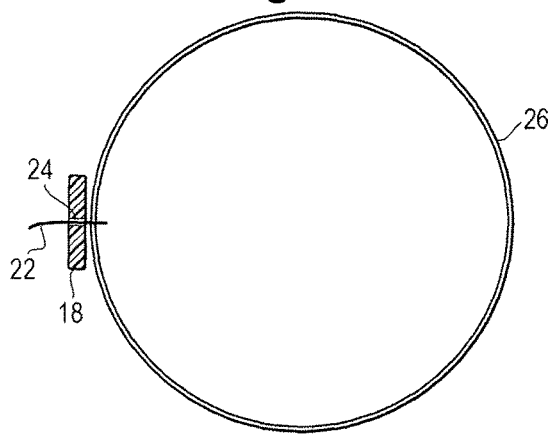
FIG. 2B illustrates a cross-sectional view of another embodiment of a pusher extension shown in FIG. 2.
Figure 2C:
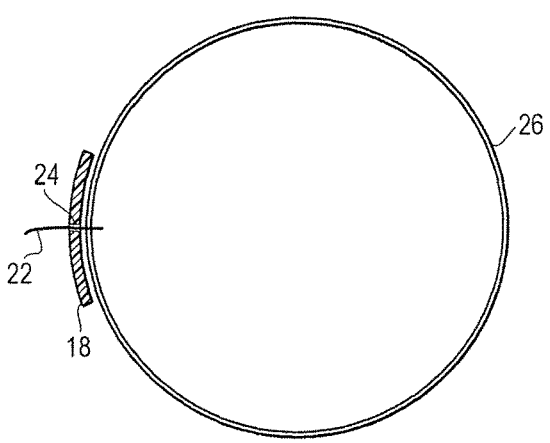
FIG. 2C illustrates a cross-sectional view of yet another embodiment of a pusher extension shown in FIG. 2.
Figure 3:
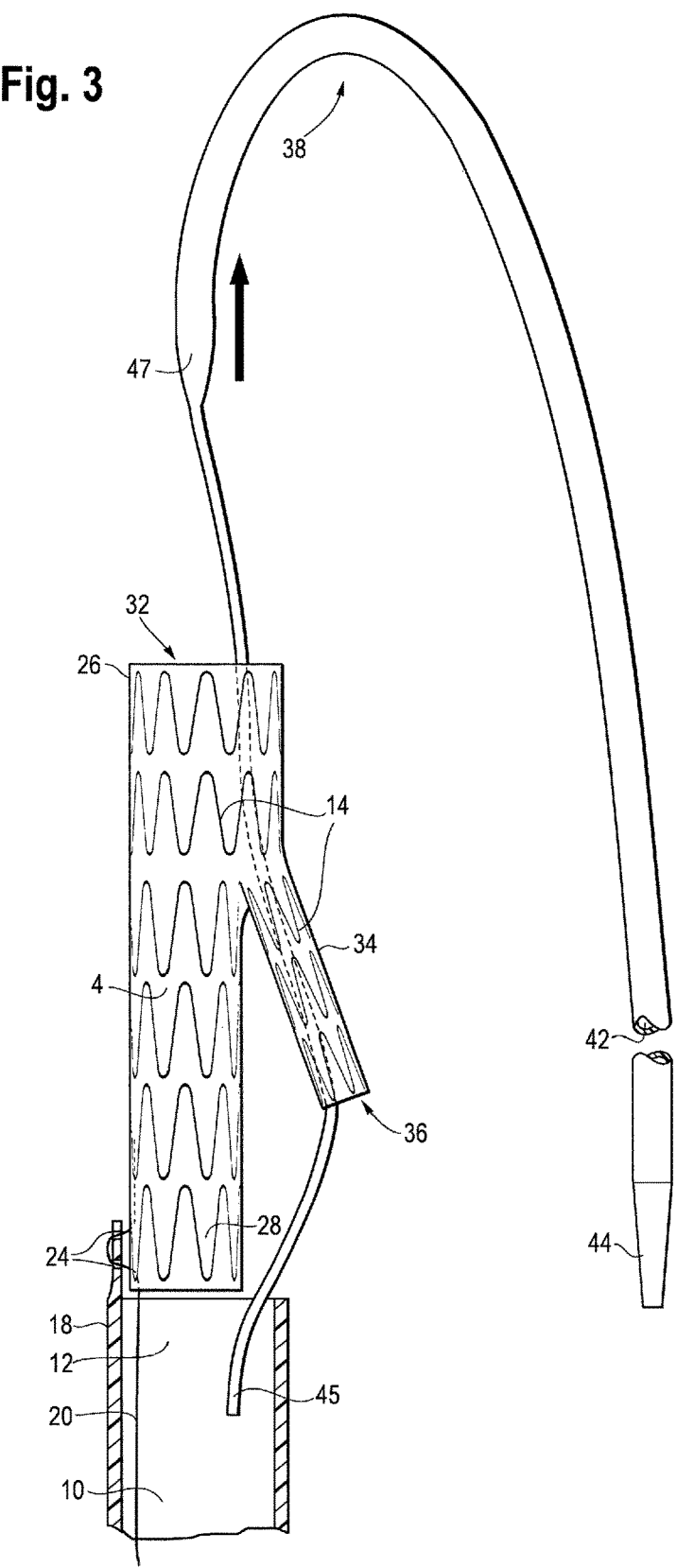
FIG. 3 shows another example of the proximal end of a delivery device with a pusher extension releasably secured to the distal end of a stent graft and an extension dilator extending proximally from the proximal end of the stent graft.

More specifically, as shown in FIG. 1A, the device 2 includes a pusher catheter 10 having a proximal end portion 12 and a distal end portion (not shown). In one example, the pusher catheter 10 has at least one lumen extending between the proximal end 12 and distal end portions. A sleeve or sheath 16, which may be manipulated through use of the distal handle 8 is preferably mounted co-axially over the pusher catheter 10. In the ready-to-deploy position, the sheath 16 extends proximally to cover the stent graft 4 as shown in FIG. 1A. As illustrated in FIGS. 2 and 3, however, the sheath 16 is removed to expose the stent graft 4 and to show detail of the proximal end 6 of the delivery device 2. The handle 8 at the distal end of the pusher catheter 10 enables manipulation of various components of the device 2.

As shown in FIG. 1A, a pusher extension 18 extends proximally of the proximal end 12 of the pusher 10. The pusher extension 18 may be continuous and/or integrally formed with the pusher 10, or it may be a separate component that is secured to the pusher 10. The pusher extension 18 may be constructed of urethane or vinyl, for example, and may be the same or a different material than the pusher 10, or the pusher extension 18 may be constructed from nitinol or stainless steel which is then connected to the pusher 10. In one example, the pusher extension 18 may include a collar at its distal end that fits around the circumference of the proximal end 12 of the pusher. Alternatively, the pusher extension 18 may be secured to the proximal end of the pusher 10 by various other acceptable attachment means including adhesives, welding, mechanical attachments, threads, snap-fits and the like. The pusher extension 18 may be generally shaped as a rod or post that extends proximally from the proximal end 12 of the pusher 10. Alternatively, the pusher extension 18 may be curved in a way so that is has a generally cross-sectional C-shape to conform or contour to the outer shape of the outer surface of the stent graft body 30.

The pusher extension 18 may be secured to the proximal end 26 of the stent graft 4, the distal end 28 of the stent graft 4, or secured to both the proximal and distal ends of the stent graft 4. In one example, the pusher extension 18 is external to the stent graft 4 and extends along the external surface of only one side of the stent graft 4. The pusher extension 18 may be secured to the stent graft 4 by one or more trigger wires, sutures, or other attachment mechanisms suitable for releasably securing the pusher extension 18 to at least a portion of the stent graft 4. It can be seen in FIGS. 1A and 2 that the pusher extension 18 extends proximally along one side of and external to the stent graft 4 to a location adjacent the proximal end 26 of the stent graft 4. As shown there, both the proximal end 26 and distal end 28 of the stent graft 4 are releasably secured to the pusher extension 18 by one or more trigger wire(s). For example, a trigger wire 20 may extend proximally through the lumen of pusher 10 and weave through one or more apertures 24 formed in the pusher extension 18 and through the stent graft 4 at the distal end 28 of the stent graft 4. The same trigger wire 20 or a different trigger wire 22 may extend further proximally and weave through one or more apertures 24 formed in the pusher extension 18 and through the proximal end 26 of the stent graft 4.

Alternatively, as shown in FIG. 3, the pusher extension 18 extends proximally along one side of and external to the stent graft 4 to a location adjacent the distal end 28 of the stent graft 4. Although, it is contemplated that the pusher extension 18 may extend to and be attached to any one or more points or locations between the proximal end 26 and the distal end 28 of the stent graft 4, including any one or more intermediate points along the body 30 of the stent graft between the proximal and distal ends 26, 28. As shown in FIG. 3, only the distal end 28 of the stent graft 4 is releasably secured to the pusher extension 18 by one or more trigger wire(s). For example, a trigger wire 20 may extend proximally through the lumen of the pusher 10 and weave through one or more apertures 24 formed in pusher extension 18 adjacent the distal end 28 of the stent graft 4. The trigger wires 20, 22 may also be releasably attached to one or more stents, suture loops (not shown) or other similar mechanisms that are secured to or part of the graft fabric. As such, the one or more trigger wires 20 and/or 22 releasably secure the proximal end 26, the distal end 28, or both, of the stent graft 4 to the pusher extension 18 at one or more points. Upon distal retraction of the trigger wire(s) 20, 22 during delivery and deployment, the stent graft 4 may be released from the pusher extension 18 as will be described in detail below. The proximal and/or distal ends 26, 28 of the stent graft 4 may be released from this retention arrangement by releasing the one or more mechanisms (i.e. releasing a trigger wire 20, 22 or any other type of mechanisms that may be used in combination with or in place of such trigger wires) during deployment of the graft 4, thereby facilitating at least partial deployment of the stent graft 4 within a vessel lumen.

While the stent graft 4 is described herein as being releasably secured to the pusher extension 18 by one or more trigger wires, other mechanisms for releasably coupling the stent graft 4 to the pusher extension 18 alone or in combination with the above-mentioned trigger wire(s) 20, 22 may also be utilized as would be recognized by one of skill in the art. In one example, a removable clip or clamp (not shown), that may be spring-loaded or otherwise "triggered" may be used to releasably couple the stent graft 4 to the pusher extension 18. The clip or clamp may be biased in a closed configuration or it may be captured and held closed using at least one trigger wire to keep the clamp closed about the stent graft 4 to releasably retain the stent graft 4 against the pusher extension 18 at one or more points between the proximal and distal ends 26, 28 of the stent graft. In another example, one or more lasso or loop arrangements (not shown) formed from wire, string or other similar filament may be used at one or more points along the length of the stent graft 4 to couple the stent graft 4 to the pusher extension. The pusher 10 may have an additional lumen through which the lasso can extend proximally, then wrap around the stent graft 4 and then extend back distally through the pusher lumen. In yet another example, a pincer mechanism (not shown) with hinged arms may be used to pinch the stent graft 4 against the pusher extension 18. When using a pincer mechanism, it may be desirable that at least 30 degrees of arc length (or more) about the circumference of the stent graft 4 is captured by the pincer. The pincer arms may be biased in a closed configuration or they may be captured and held closed using at least one trigger wire to keep the arms closed about the stent graft 4. When the one or more trigger wires are removed, the pincer arms may release the stent graft 4 from the pusher extension 18.

In a further example, a trigger wire may be spirally wrapped (not shown) along an axial length of the stent graft 4 to capture the entire circumference of the stent graft and releasably couple it to the pusher extension at one or more points, such as by weaving through the one or more apertures 24 formed in the pusher extension. By capturing the entire circumference of the stent graft and/or by providing a greater number of spiral wraps about the stent graft 4, the user may have greater control of the positioning and release of the stent graft 4 from the pusher extension 18. A break or gap in the spiral capture can be made to accommodate the side branch 34 and/or any fenestration or ostium formed in the stent graft 4. The spirally wrapped trigger wire may then be re-inserted into the pusher lumen and extend distally to the handle 8 for manipulation by the user. Removal of the spiral trigger wire may serve to release the stent graft 4 from the pusher extension 18. In another example, one or more trigger wires may be used to attach the stent graft 4 to the pusher extension 18 such as by weaving the trigger wire(s) 20, 22 through one or more holes or apertures 24 formed in the pusher extension 18 proximal to the distal end of the stent graft 4 (as shown in FIGS. 2 and 3, for example). The one or more apertures 24 are separated by a predetermined arc length to allow the trigger wire(s) 20, 22 to weave through the pusher extension 18, then through one or more longitudinally spaced points located along the body 30 of the stent graft 4 and/or circumferentially around the body 30 of the stent graft 4 and if desired, weave back through the pusher extension 18 to releasably couple the stent graft 4 to the pusher extension 18 at one or more points. Removal of the trigger wire(s) facilitates release of the stent graft 4 from the pusher extension 18.

The stent graft 4 carried on the device 2 preferably has a substantially tubular main body 30 having a proximal end 26 and a distal end portion 28 with a main lumen 32 extending through the main body 30. A side branch 34, also preferably having a substantially tubular body defining a lumen 36, preferably extends from the main body 30 and may be integrally formed with the main body, or alternatively, the side branch 34 may be a separately formed component that is secured to the main body 30 such as by stitching, bonding, adhesive or the like. The lumen 32 of the main body and the lumen 36 of the side branch are preferably in fluid communication. In one example, both the main body 30 and the side branch 34 are constructed from one or more biocompatible materials including, but not limited to, polyesters, fluorinated polymers and polyurethanes and/or may be made from natural or organic materials. The materials may also be subjected to surface modifications or coatings. The graft 4 including the side branch 34, preferably includes one or more stents 14 secured to the graft material. The stents 14 may be attached to the inside, the outside, or both of the graft material and may be self-expanding, mechanically expandable, or a combination thereof.

In a preferred example, the stent graft 4 is configured to be deployed into the vasculature of a patient with the main body 30 being located in the common iliac artery and the side branch being directed towards an internal iliac artery of the common iliac artery, although other stent graft configurations for deployment into various other body vessels are also contemplated depending on various factors including, but not limited to, the particular vessel(s) being treated and/or the location of a particular damaged or diseased portion of a vessel.

As shown in FIG. 1A, an extension dilator 38 extends proximally from the proximal end 40 of the sheath 16. The extension dilator 38 has a proximal tip 44 and a distal end 45 and a lumen 42 extending therebetween, and is preferably flexible yet stiff enough to allow it to be navigated and advanced through a patient's vasculature. As shown in FIGS. 1-3, at least a portion of the extension dilator 38 may be curved in a hook or U-shaped configuration. However, the extension dilator 38 may have a variety of shapes and configurations depending on the procedure being performed and the vasculature through which the delivery device 2 is being navigated. As FIG. 1A illustrates, the distal end 45 of the extension dilator may terminate at a point adjacent or near the proximal end 12 of the pusher 10, or the distal end 45 of the extension dilator 38 may extend further distally within the lumen of the pusher 10. In another example, the distal end 45 of the extension dilator 38 may extend distally through the lumen of the pusher 10 to the external manipulation section or handle 8 of the delivery device 2. In yet another example, an inner cannula (not shown) may extend from the handle 8 and mate with the distal end 45 of the extension dilator 38.

The delivery device 2 preferably includes or is pre-loaded with the extension dilator 38. This extension dilator 38 extends proximately from its distal end 45 within the lumen of the pusher 10 and runs along the outside of the distal end 28 of the stent graft 4, and into the lumen 36 of the side branch 34. The extension dilator 38 continues to run proximally through the lumen 36 of the side branch 34, out of the proximal end 26 of the main graft lumen 32 and extends proximally from the proximal end 40 of the sheath 16. The lumen of the extension dilator 38 is preferably large enough to accept a 0.035 inch guide wire there within. While the extension dilator 38 is releasably secured to the proximal end 40 of the sheath 16 such as by friction fit, the extension dilator 38 may be manipulated and/or moved, either longitudinally or rotationally, independently from other components of the delivery device 2 at one or more stages of a delivery and deployment procedure, such as to facilitate cannulation of a branch vessel, for example, as will be described in further detail below. The extension dilator 38 may be constructed of various biocompatible materials such as urethane and vinyl, for example, which provides for flexibility yet sufficient rigidity to allow the device 2 to extend and navigate through a patient's tortious vasculature.

Looking to FIG. 1, one or more control mechanisms located outside of the patient's body at the distal end portion or handle 8 of the delivery device 2 allows the physician to manipulate the extension dilator 38 and, at the appropriate time during a particular procedure, release the extension dilator 38 from the delivery device 2 so that the extension dilator can be removed from the vasculature as described herein. In one example, the extension dilator 38 is free to rotate independently of the other components of the delivery device 2, including the pusher 10, the pusher extension 18, the stent graft 4 and the sheath 16. As such, the handle 8 can be acted upon to manipulate the extension dilator 38 longitudinally (in either a proximal or distal direction) or alternatively, the handle 8 can be acted upon by the user to provide rotational control of the extension dilator 38. The distal end portion or handle 8 can also be acted upon by the physician to manipulate other components of the delivery device, such as to retract sheath 16, withdraw one or more trigger wires 20, 22 or otherwise interface with any retention mechanism(s) that at least partially restrain and hold the stent graft 4 on the delivery device 2 when it is appropriate or desirable to fully deploy the stent graft 4 in the vessel lumen during a particular procedure.

The extension dilator 38 may be of a substantially constant outer diameter between its proximal tip 44 and its distal end 45, or alternatively, the outer diameter of the extension dilator 38 may vary between its proximal end 44 and distal end 45. As shown in FIGS. 1A, 2 and 3 for example, the outer diameter of the extension dilator 38 near the distal end 45 is smaller than the outer diameter of the extension dilator 38 near the proximal end 44. For example, the outer diameter of the extension dilator 38 may be in a range of about 1 Fr to about 5 Fr (and preferably not larger than about 4.1 Fr) near the distal end 45 and may be in a range of about 8 Fr to about 14 Fr (and preferably not larger than about 12 Fr) near the proximal end 44.

More particularly, the extension dilator 38 may have a smaller outer diameter, such as about 4 Fr along its length from distal end 45, through the lumen of the side branch 34 to a location near the proximal end 26 of the stent graft 4. The extension dilator 38 may then flare outwardly at point 47 to a larger outer diameter such as in a range of about 10-12 Fr, and maintain this larger diameter from point 47 to the proximal end 44, (or alternatively, the extension dilator 38 may have a short bulged region of an even larger increased diameter near point 47 and then taper back slightly radially inwardly from the bulged region toward the proximal end 44). The proximal end 40 of the sheath 16 may taper radially inwardly and thereby mate with the extension dilator 38 near the outwardly flared or bulged portion 47 to thereby provide a smooth transition between the proximal end 40 of the sheath 16 and the outer surface of the extension dilator 38. The outer diameter of the extension dilator 38 may be slightly larger than the inner diameter of the sheath 16 at the location where the extension dilator 38 and the sheath 16 mate. As such, the sheath 16 may be releasably secured to the extension dilator 38 at the point where the respective components overlap, such as by friction fit, for example, or any other mechanisms (adhesives, threads and the like) which allows the respective two components to remain connected and maintain sufficient pull-out force at the point of overlap during a portion of a procedure and then separated as necessary or desired as described further below.

As shown in FIGS. 1 and 1A, in a pre-deployment configuration, the sheath 16 extends proximally from distal or handle portion 8 and covers the stent graft 4. The sheath 16 may have an inner diameter of about 13 Fr to about 20 Fr and may taper radially inwardly at the proximal end 40. The angle of the taper of the proximal end 40 of the sheath 16 may substantially correspond with the angle or shape of the radially outwardly flared or bulged portion 47 of the extension dilator 38. As shown in FIG. 1A, the proximal end 40 of the sheath 16 is coaxial with and covers at least a portion of the flared portion 47 of the extension dilator 38 in a pre-deployment configuration, thereby creating a smooth transition between the sheath 16 and the extension dilator 38. This smooth transition has several advantages, including but not limited to facilitating atraumatic navigation of the device 2 within the vasculature while minimizing and/or substantially eliminating damage to vessel walls during delivery and deployment.

Now looking at FIGS. 4 through 14, there is schematically illustrated a series of vessels within the human body, including the common iliac arteries 48 and 50 and the respective internal iliac arteries 52 and 54. (It is noted that the respective common iliac arteries bifurcate into an internal iliac artery and an external iliac artery, however, the external iliac arteries are not identified or labeled separately from the common iliac arteries 48, 50 in this description). Thus, when the stent graft 4 is deployed within a vessel, a portion of the stent graft 4 may be expanded within the common iliac artery 48, while a distal portion of the stent graft 4 may extend into the external iliac artery. Also, the systems and methods described herein find particular application in the delivery, placement and deployment of one or more stent grafts therein, although as discussed earlier, the disclosed systems and methods are not restricted to this particular purpose and may be used in a variety of applications as will be appreciated by one of skill in the art.

While FIGS. 4-14 illustrate a method for delivery and deployment of a stent graft, this is only one example of a possible delivery scheme and should not be considered as limiting, and one of skill would recognize that the order of steps or the steps themselves could be altered, rearranged and/or steps could be eliminated while additional steps could be added and/or entirely different suitable delivery methods could be used if necessary and desired.

Figure 4:
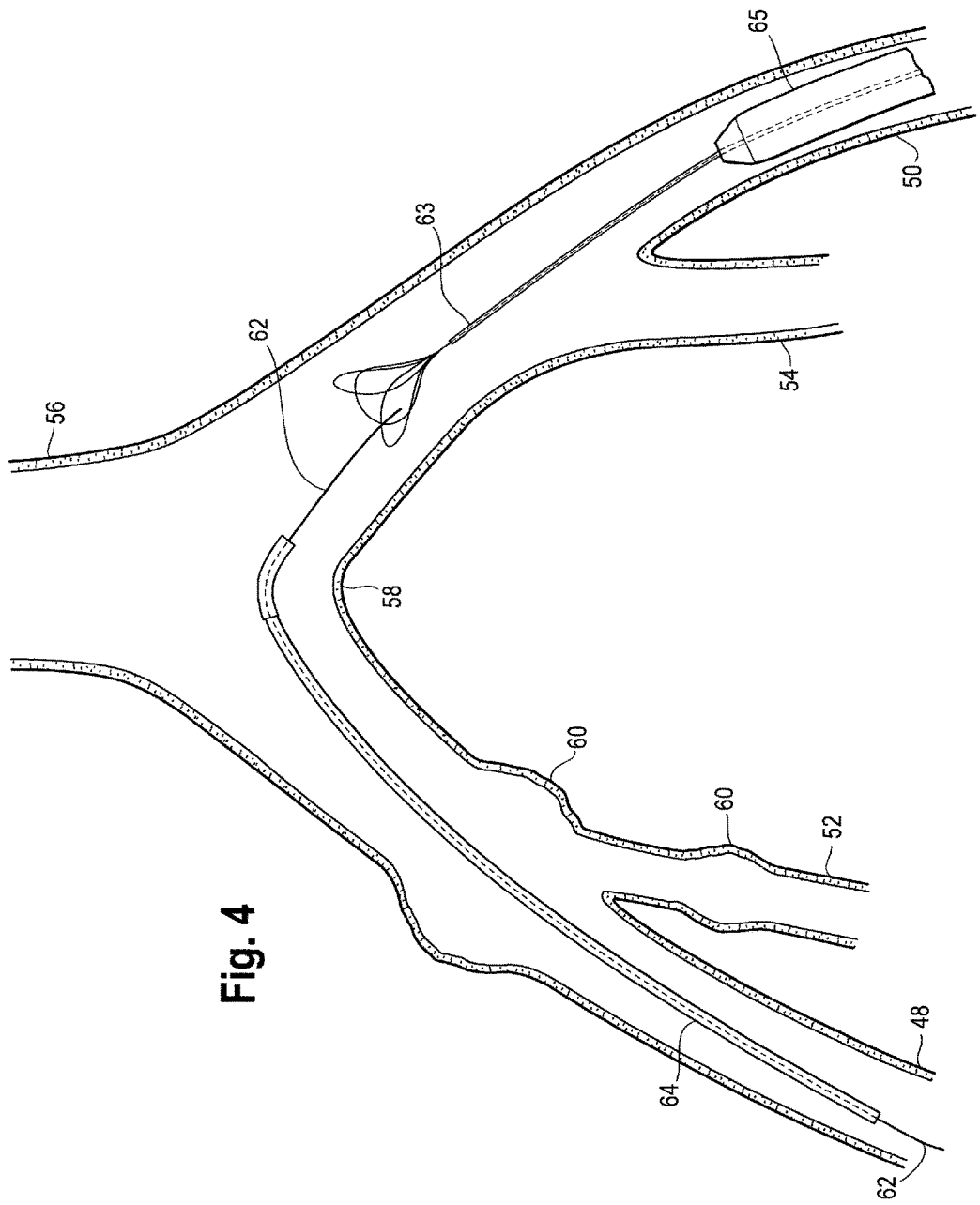

Turning to FIG. 4, a descending aorta 56 extends down to an aortic bifurcation 58 from which extend common iliac arteries 48 and 50. From each of the common iliac arteries, internal iliac arteries 52 and 54, respectively, extends. In most cases, the internal iliac arteries 52 and 54 cannot be practically accessed from their distal ends remote from the junction with the common iliac artery. For illustrative purposes, common iliac artery 48 and internal iliac artery 52 are shown as having a diseased portion, including an aneurysm 60, although, it will be appreciated that one or both common iliac arteries 48, 50 and/or one or both internal iliac arteries 52, 54 may also include diseased portions that may be treated in accordance with the systems and methods described herein.

As shown in FIG. 4, the introduction of the delivery device 2 is preferably preceded by the placement of a "through wire" 62 within the vasculature of a patient, which provides an "up and over" pathway (i.e. a pathway extending proximally up through the contralateral iliac artery 50, over the aortic bifurcation 58 and distally down the ipsilateral common iliac artery 48). The pathway provided by the through wire 62 may be used to ultimately facilitate the introduction and placement of the delivery device 2 in a desired location with a vessel lumen, such as providing a pathway over which the delivery device 2 may be tracked or extended, for example.

The through wire 62 may be placed in the vasculature by various acceptable methods and techniques, and introduced through various locations. In one non-limiting example, the through wire 62 may be introduced into a femoral artery via a femoral incision (not shown) and extended proximally beyond the aortic bifurcation 58 to the descending aorta 56. A snare 63 may be tracked through an auxiliary sheath 65 in the contralateral iliac artery 50, and the through wire 62 snared by snare 63 and pulled from the contralateral side to create the "up and over" pathway. Alternatively, the through wire 62 may be introduced into the vasculature through other locations, including, but not limited to through a brachial puncture (not shown) for placement in a desired location within the iliac arteries. As shown in FIG. 4, a portion of the through wire 62 extends through the lumen of an auxiliary sheath 64 that is temporarily positioned in the ipsilateral iliac artery 48. The auxiliary sheath 64 may be removed after the through wire 62 has been snared and is properly in place. Placement of the through wire 62 as shown in FIG. 4 by any number of acceptable techniques and methods aids in the introduction of the delivery device 2 into the patient's vasculature as described in further detail below.

Figure 5:
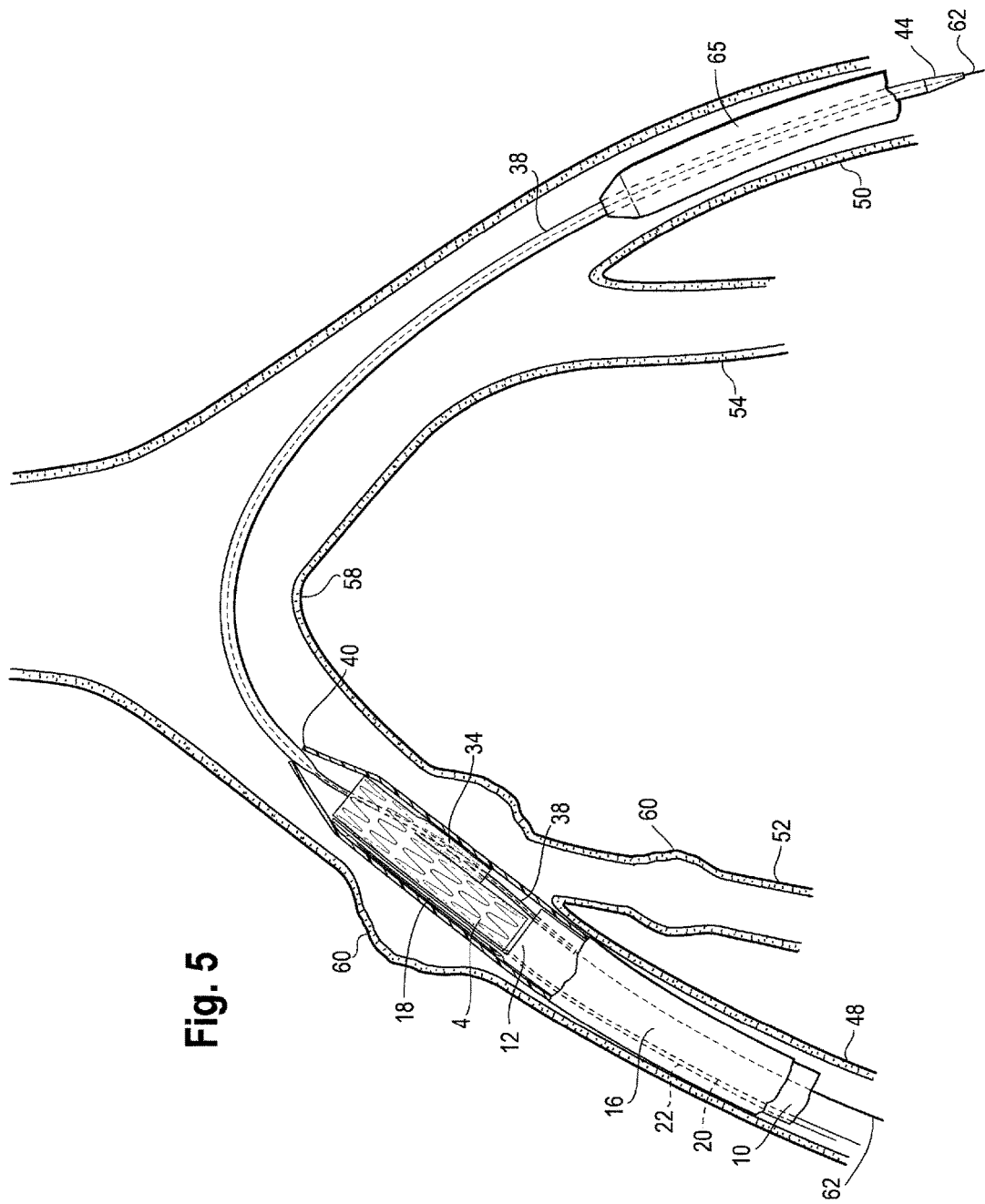

As shown in FIG. 5, the device 2 may be introduced into the common iliac artery 48 and advanced over the through wire 62 with the proximal end 40 of the sheath 16 located near the aortic bifurcation 58. Preferably, the device 2 is advanced so that the extension dilator 38 extends over the aortic bifurcation 58 and is tracked distally through the contralateral iliac artery 50 and through the auxiliary sheath 65 that remains in place in the contralateral iliac artery 50. At this stage, sheath 16 covers the branched stent graft 4 that is carried on the device 2. With the device 2 in this position within the lumen of common iliac artery 48, the graft 4 (enclosed within the sheath 16) is preferably adjacent to the opening of the internal iliac artery 52.

Figure 6:
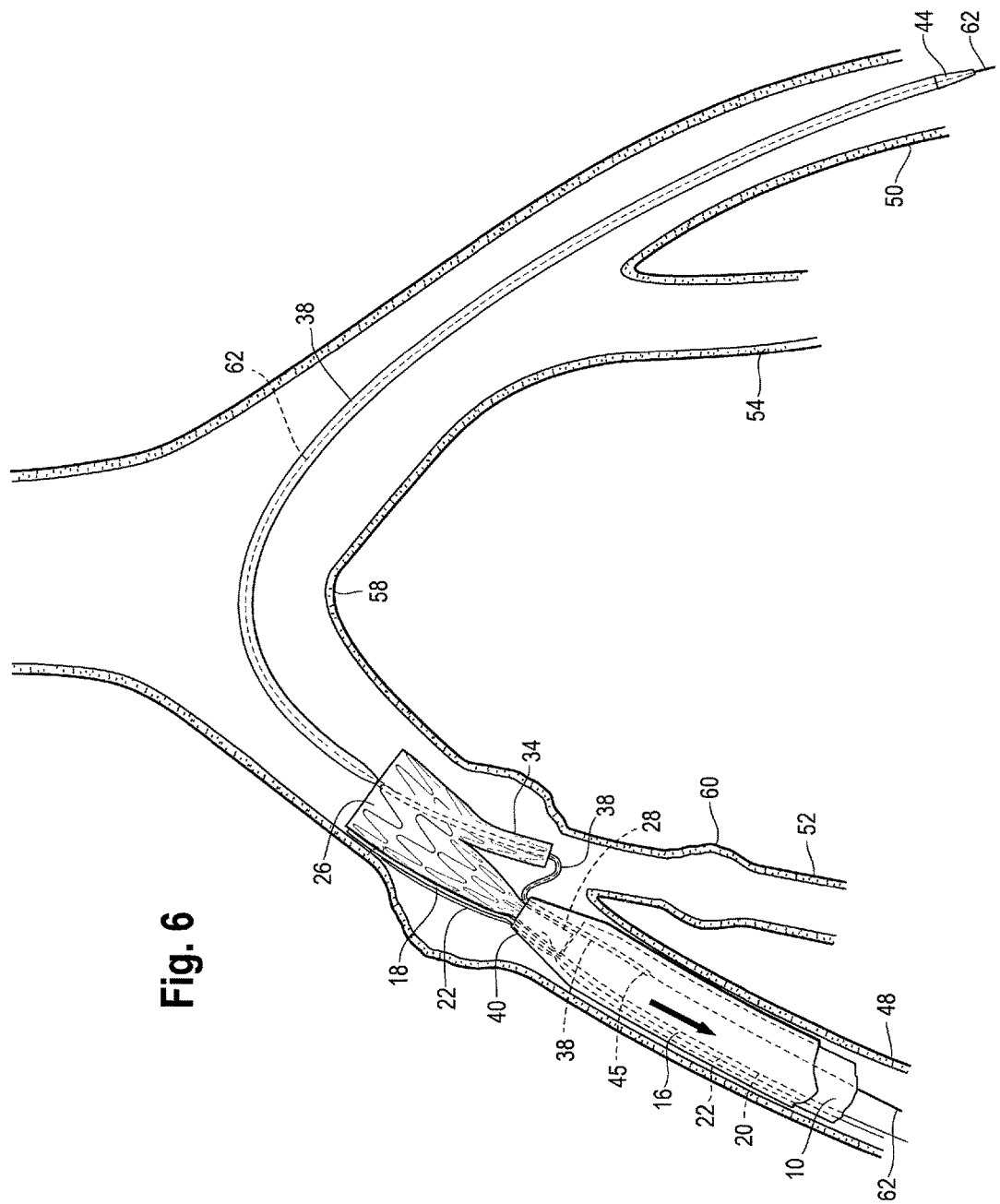

As shown in FIG. 6, the sheath 16 has been partially withdrawn (in a distal direction) to expose the proximal end 26 of the stent graft 4 and the side branch 34 of the stent graft 4. Where sheath 16 has a tapered proximal end 40, this distal retraction of sheath 16 causing it to separate from the extension dilator 38 and expose at least a portion of the stent graft 4 may require a force applied by the user's hand. During separation of sheath 16 from the flared or bulged portion 47 of the extension dilator 38, the tapered proximal end 40 of sheath 16 may deform radially outwardly as the respective components slide past one another.

The stent graft 4 is partially unconstrained in that a proximal end 26 and side branch 34 has been freed from the confines of the sheath 16, but it is still preferably retained by a retention mechanism at one or both of the proximal end 26 and distal 28 ends of the stent graft, including, but not limited to the trigger wires 20 and/or 22 that releasably secure the stent graft 4 to the pusher extension 18, as shown and described in connection with FIG. 2 and/or FIG. 3 set forth above. The graft may also include constraints or diameter reducing ties in the central portion, if desired. Accordingly, the stent graft 4 is not yet in a fully expanded condition within the lumen of the common iliac artery 48.

It can be seen in FIG. 6 that the stent graft 4 carried on the device 2 is pre-loaded in one exemplary arrangement. More specifically, the device 2, with the stent graft 4 carried thereon, is pre-loaded with the extension dilator 38 which extends over the through wire 62 from its distal end 45, through the lumen at the proximal end 12 of pusher 10, through the lumen 36 of the side branch 34 of the stent graft, out of the proximal end 26 of the main graft body 4 and over the through wire 62 to its proximal tip 44 which has been located in the contralateral iliac artery 50. However, it is also contemplated that the device can be pre-loaded in a variety of acceptable ways that may not only aid in the placement and deployment of the main stent graft 4 in the common iliac artery but which also ultimately facilitates the placement of one or more additional stent grafts into the branched vessels, including, but not limited to, the internal iliac artery.

Figure 7:
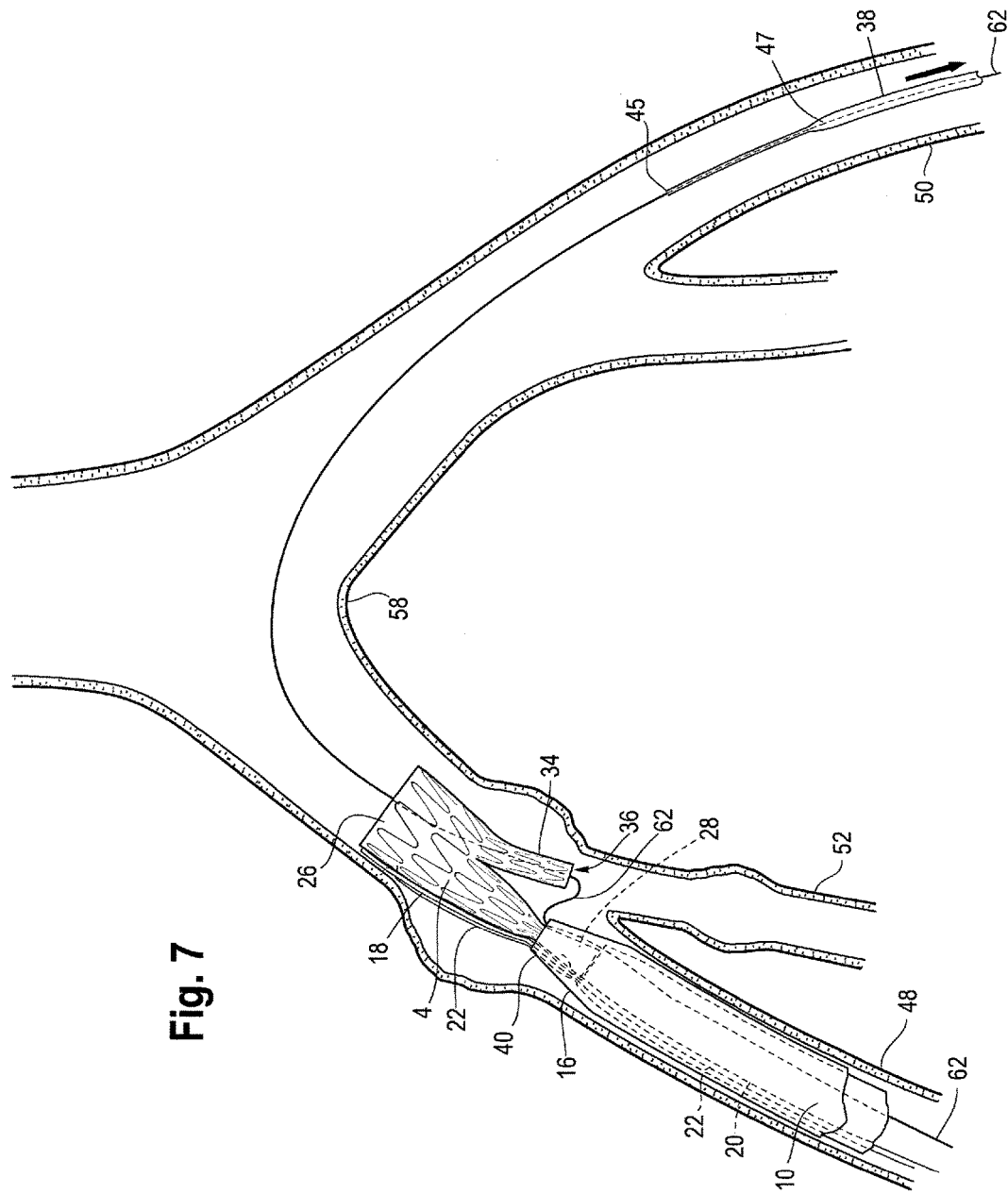

FIG. 7 shows an example of the next stage of a graft delivery and deployment sequence where the extension dilator 38 may be separated from the sheath 16 and removed from the patient's vasculature. In one example, the control mechanism located outside of the patient's body at the distal end portion 8 of the delivery device 2 can be manipulated by the physician, so as to release the extension dilator 38 from the sheath 16, thus allowing the extension dilator 38 to be separated from the device 2 and removed from the vasculature.

In one example, the user may push the extension dilator 38 forward or proximally to separate it from the sheath 16. Alternatively, the user may hold the extension dilator 38 steady and in a fixed position within the vessel while simultaneously retracting the sheath 16 in a distal direction to separate the sheath 16 from the extension dilator 38. The extension dilator 38 may be withdrawn distally (as shown by the arrow in FIG. 7) from the contralateral iliac artery 50, although, if desired or necessary, the extension dilator 38 may be withdrawn by other acceptable techniques and methods, and/or withdrawn through other locations. Although auxiliary sheath 65 has been removed from FIG. 7 for purposes of clarity, if the auxiliary sheath 65 is still in place within the iliac artery 50, the extension dilator 38 may be withdrawn through the auxiliary sheath 65. With the extension dilator 38 removed, the through wire 62 preferably remains in place such that it extends through the delivery device 2 (in the ipsilateral iliac artery 48), out the proximal end 26 of the main graft body 4, over the aortic bifurcation 58 and distally through the contralateral iliac artery 50. As has been described, the through wire 62 allows a physician to track a delivery device 2 to a desired location within the patient's vasculature, manipulate and place a stent graft 4 therein, such as in a common iliac artery. The same through wire 62 may also facilitate the introduction of additional stent grafts in a branched and/or side vessel, as further described below.

Figure 8:
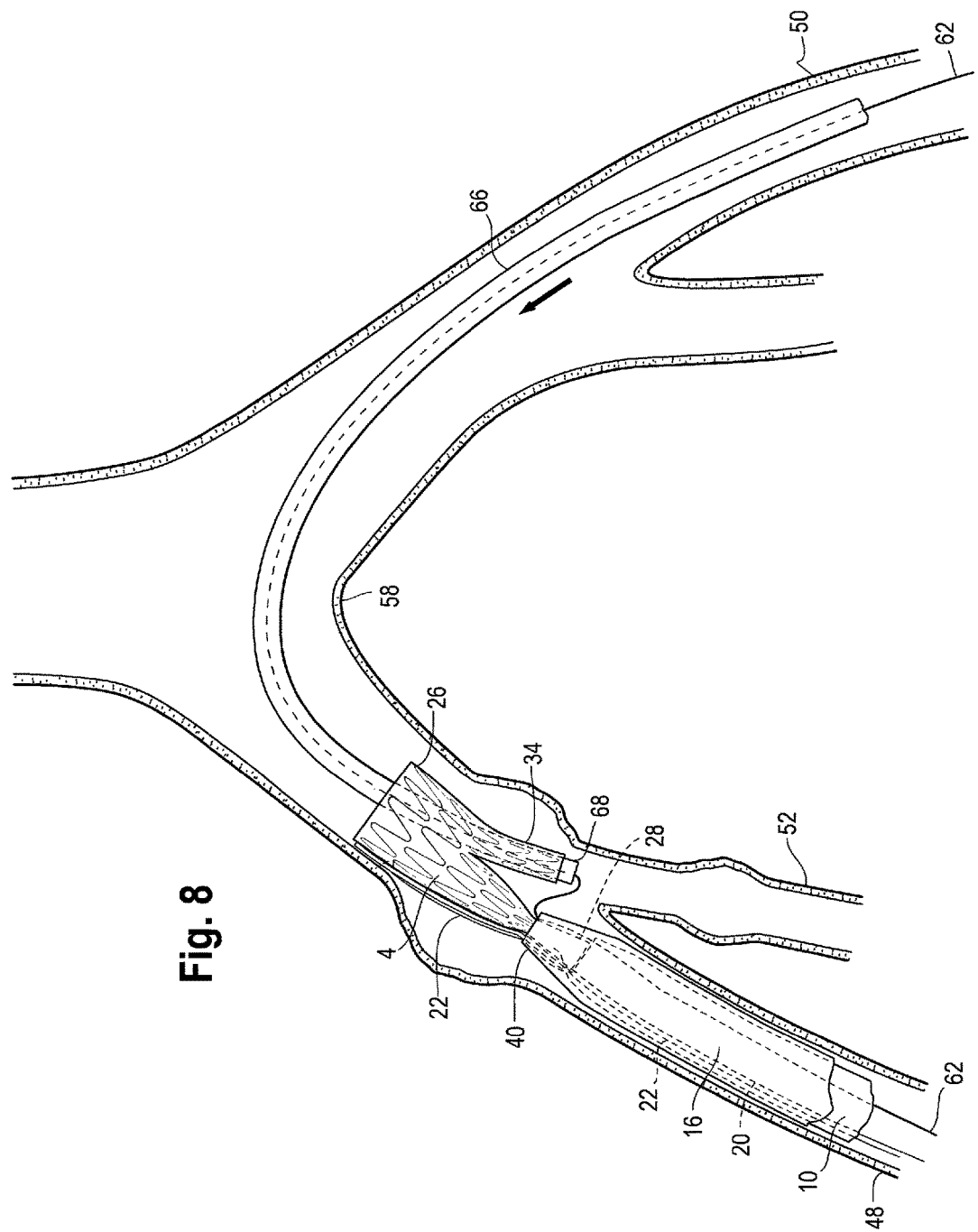

At this stage, illustrated generally in FIG. 8, an additional "up and over sheath" or "contralateral auxiliary sheath" 66 is introduced into the patient's vasculature, which is preferably intended to facilitate the delivery and deployment of an extension graft 78 into the ipsilateral internal iliac artery 52. As illustrated in FIG. 8, a contralateral "up and over" auxiliary sheath 66 may be extended proximally through the contralateral iliac artery 50, over the aortic bifurcation 58, into the proximal end 26 of the main graft body 4 and through the lumen 36 of side branch 34. This may be accomplished by tracking the "up and over" contralateral auxiliary sheath 66 over the pathway provided by the through wire 62 which is still in place in the iliac arteries 48, 50. As FIG. 8 best shows, the contralateral sheath 66 is extended until the tip 68 of the sheath 66 emerges from the distal end of the side branch 34 such that the tip 68 is adjacent to the opening of the internal iliac artery 52.

Figure 9:
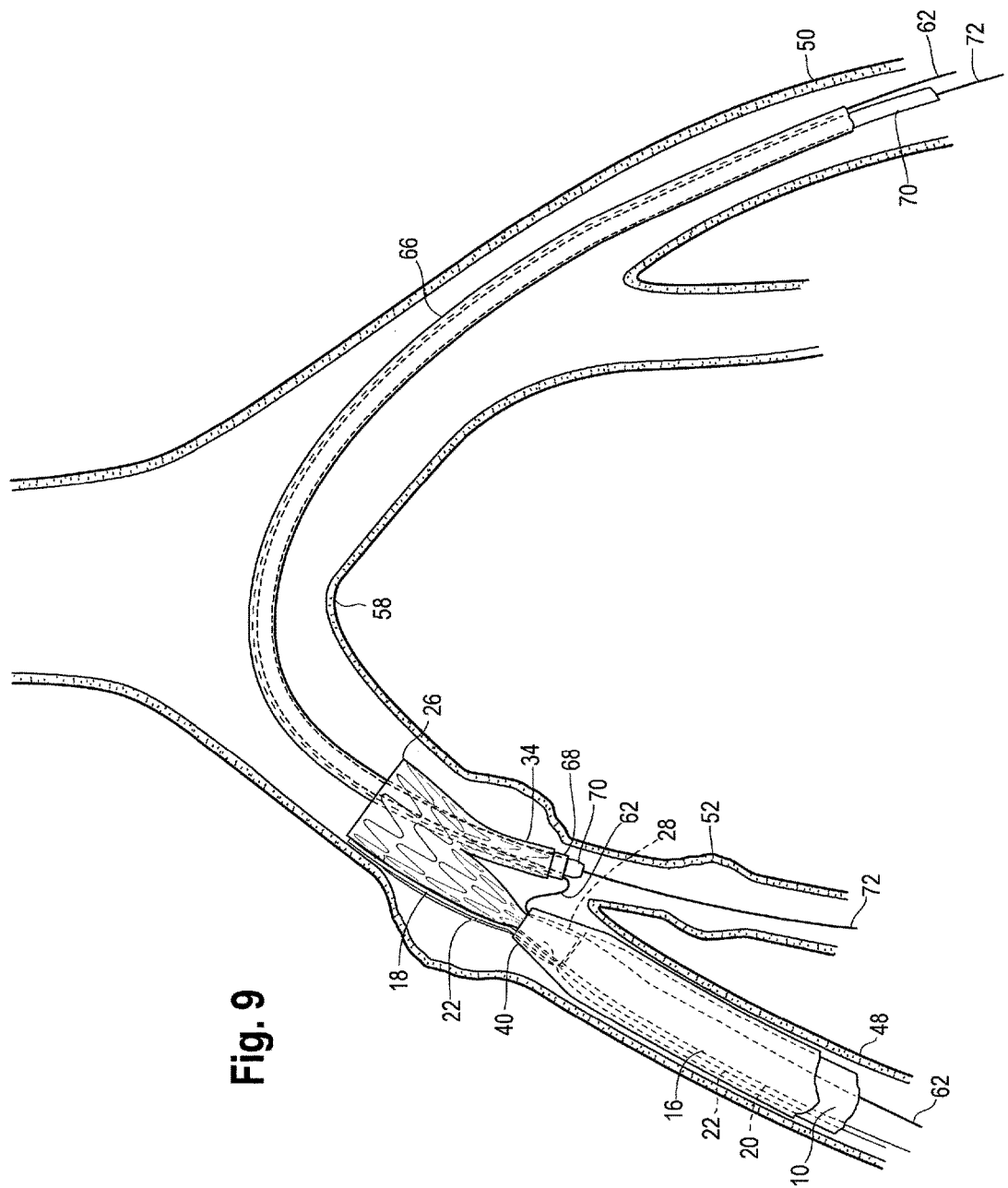

Auxiliary catheter 70, with an auxiliary wire 72 extending longitudinally through the lumen thereof, may be advanced all the way through the contralateral sheath 66 for cannulation of the internal iliac artery 52, as shown in FIG. 9. If necessary or desired, auxiliary wire 72 that is initially introduced into the internal iliac artery 52 (as shown in FIG. 9) may be replaced with an alternative, stiffer auxiliary wire which may then be extended further, along with the auxiliary catheter 70, into the internal iliac artery 52.

Figure 10:
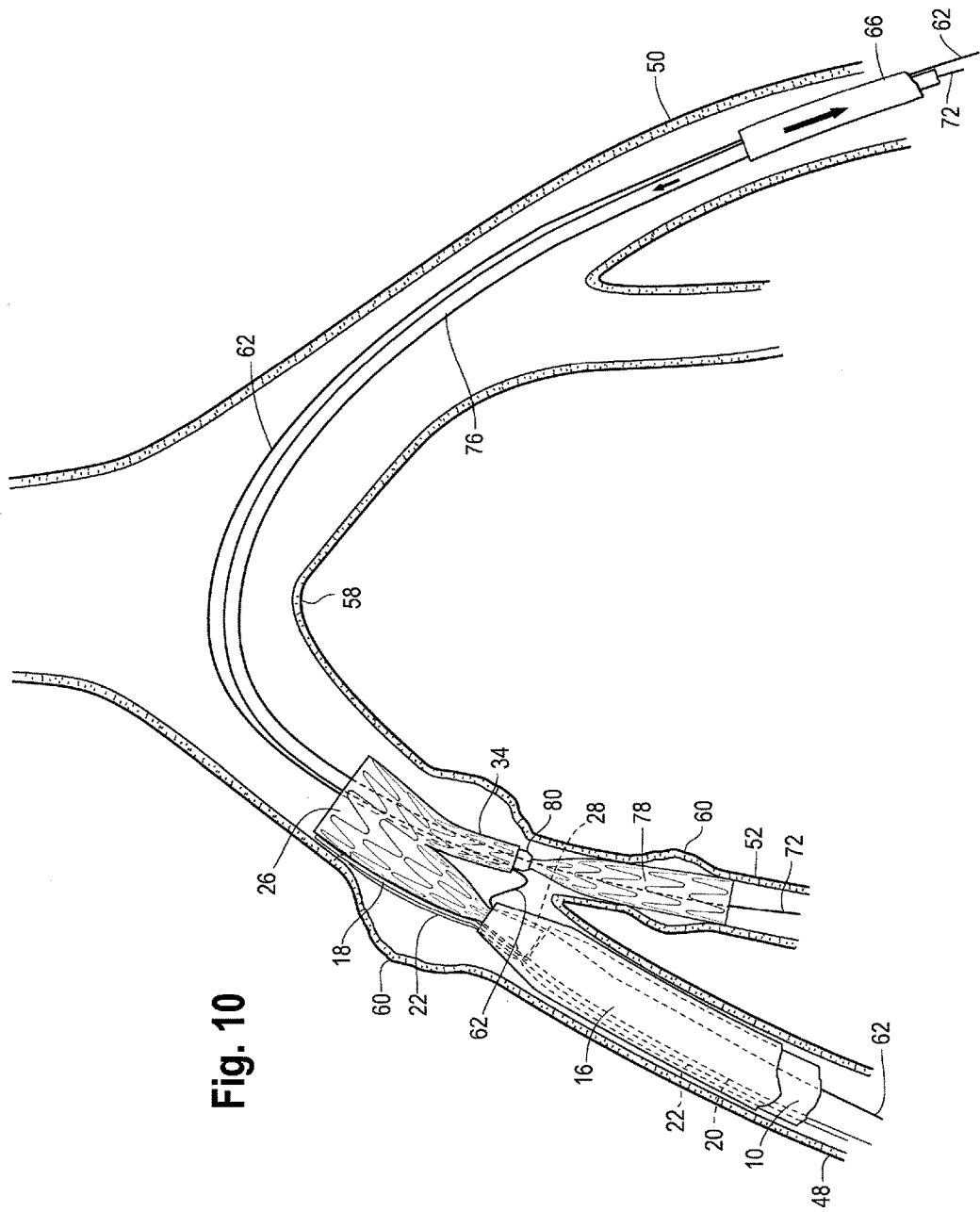

With the auxiliary wire 72 extended into and placed in a desired location in the internal iliac artery 52, the auxiliary catheter 70 can be withdrawn from the patient's vasculature. In one example, the auxiliary catheter 70 can be pulled distally through the contralateral iliac artery 50 and removed from the vessel. However, the auxiliary wire 72 remains in place after the auxiliary catheter 70 has been removed from the patient's body. At this stage, a second delivery device 76 can be tracked over the pathway provided by the auxiliary wire 72. As shown in FIG. 10, the second delivery device 76 preferably carries an additional leg or "extension" stent graft 78 that is intended for delivery and deployment within the internal iliac artery 52, although extension graft 78 may be deployed within any portion of the patient's vasculature as necessary or desired. The extension graft 78 is preferably carried on a proximal end portion of the second delivery device 76, while a distal external manipulation portion (not shown) remains outside of the patient's body and allows a physician to manipulate the second delivery device 76 within the patient's vasculature. The extension graft 78 is preferably covered by an appropriately sized sheath during delivery. As shown in FIG. 10, the second delivery device 76 is tracked through the sheath 66 and over the auxiliary wire 72 until the proximal end 80 of the second delivery device 76 is extended beyond the distal end of the side branch 34 and into the internal iliac artery 52, and the extension graft 78 positioned in a desired location therein. Preferably, the extension graft 78 is positioned in the internal iliac artery 52 so that it extends both proximally and distally away from the location of an aneurysm that may be present, therefore, spanning and bypassing the diseased portion of the vessel.

Figure 11:
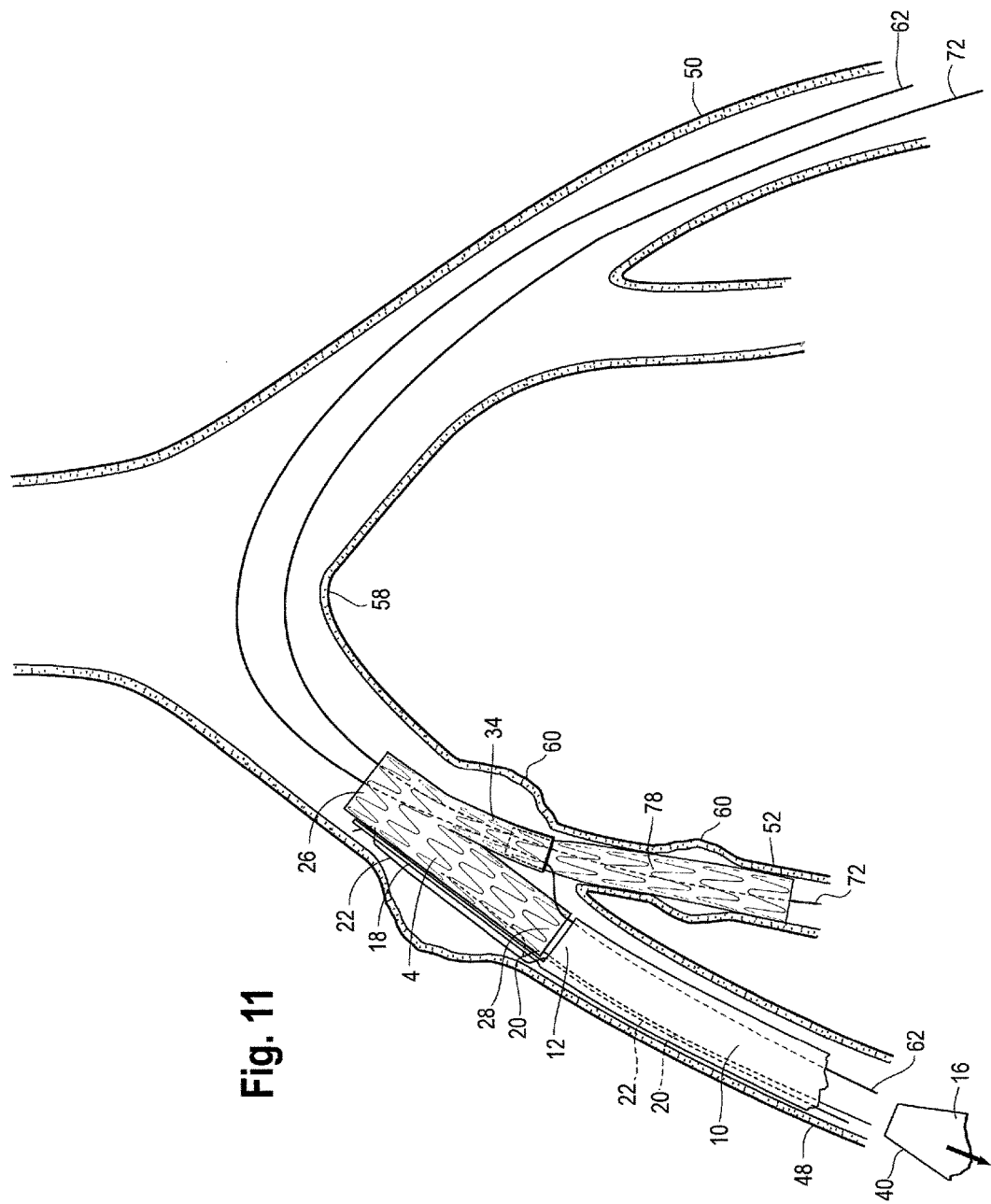

As shown in FIG. 11, the extension graft 78 may then be deployed within the lumen of the internal iliac artery 52. For example, the sheath (not shown) covering the extension graft 78 on the second delivery device 76 may be withdrawn by pulling the sheath distally through the contralateral iliac artery 50 for removal from the patient. The second delivery device 76 may also be removed from the patient's vasculature by pulling the second delivery device 76 distally through the contralateral iliac artery 50. The auxiliary wire 72 may also be removed from the internal iliac artery 52, such as by pulling it distally from the contralateral iliac artery 50.

As further shown in FIG. 11, the sheath 16 which covered the stent graft 4 prior to delivery and deployment may be withdrawn by pulling the sheath 16 distally from the ipsilateral common iliac artery 48 to expose the distal end 28 of the stent graft 4. After removal of the sheath 16, the stent graft 4 is at least partially deployed within the vessels 48, 52. However, one or more additional retention mechanisms, such as trigger wire 20 and/or trigger wire 22 are still present, which releasably retain the proximal end 26, the distal end 28 (or both ends) of the stent graft 4 to the pusher extension 18.

Figure 12:
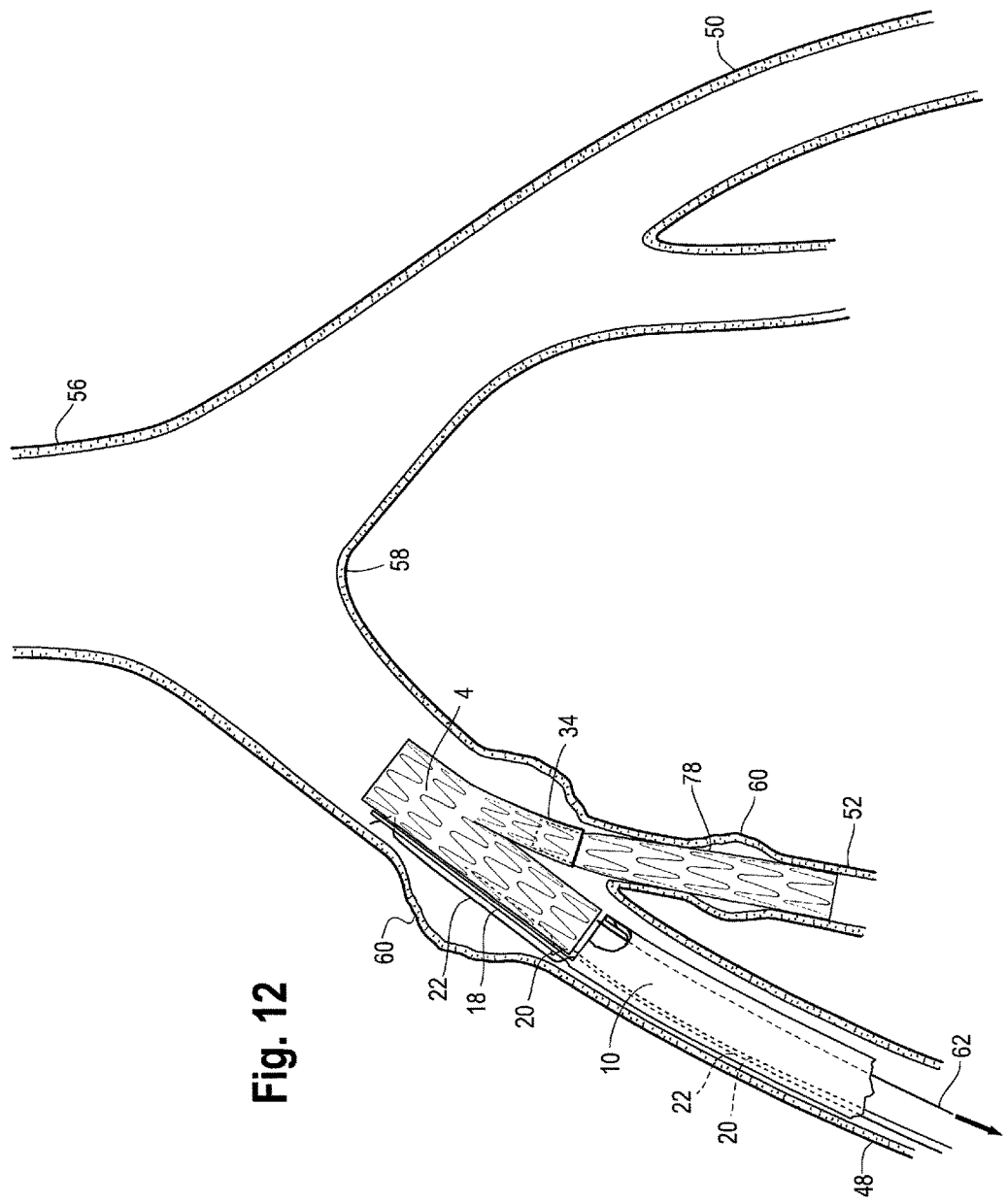

As shown in FIG. 12, the through wire 62 may be retracted distally through the proximal end 26 of the stent graft 4 and through the lumen 36 of the side branch 34 until the proximal end of the through wire 62 is located distal to the distal end 28 of the stent graft 4. At this time, the through wire 62 may then be again manipulated by the user to push it proximally back up into the lumen 32 of the main body 30 of the stent graft 4 and out through the proximal end 26 of the stent graft 4 until it extends into the descending aorta 56, as can be seen in FIG. 13.

Figure 13:
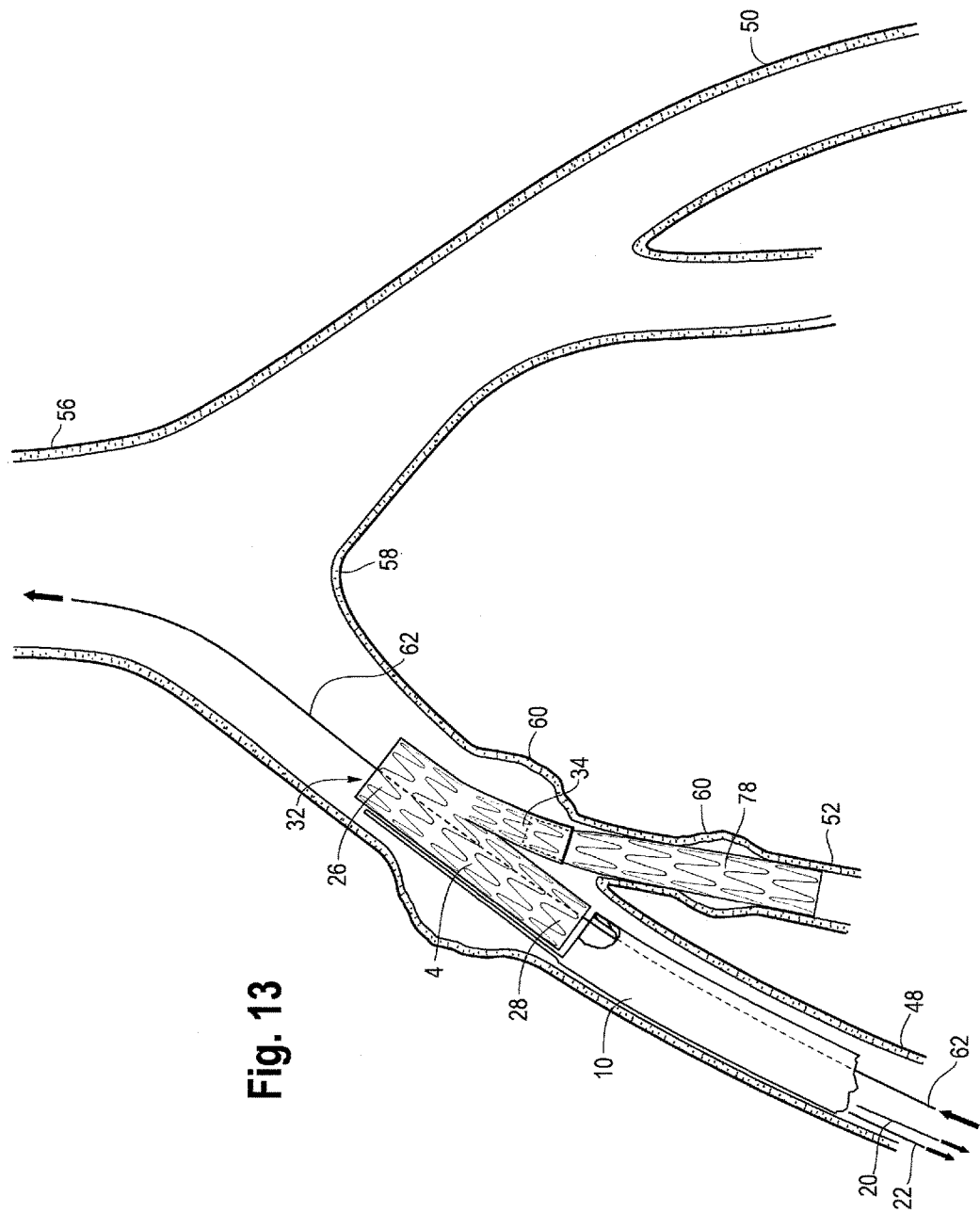

At this time, one or more retention mechanisms that releasably secure the stent graft 4 to the delivery device 2 may be removed, including but not limited to removal of trigger wire 20 and/or trigger wire 22 which retain the stent graft 4 to the pusher extension 18 as shown in FIG. 13. To accomplish removal of the retention mechanism(s) when it is appropriate or desirable to fully deploy the stent graft 4 in the vessel lumen 48 during a particular procedure, one or more control mechanisms located on the distal handle portion 8, can be acted upon by the physician to manipulate and remove one of the trigger wire(s) and/or other retention mechanism(s). Once the retention mechanism(s) have been removed from the proximal and/or distal ends 26, 28 of the stent graft 4 (and/or from extension graft 78 if such retention mechanisms are present in the second delivery device 76), the respective grafts 4, 78 may be radially expanded or deployed within the respective vessels 48, 52. Proximal and/or distal retention (not shown) of extension graft 78 may include the same or similar retention mechanisms as those described above in connection with the retention of stent graft 4 on delivery device 2, such that extension graft 78 may be retained on the second delivery device 76 in a manner similar to that of graft 4. Of course, other types and methods of proximal and/or distal restraint of extension graft 78 may be used including various diameter reducing ties, fasteners or the like that are suitable for removably securing the extension graft 78 onto delivery device 76. Proximal and/or distal retention of extension graft 78 may be in addition to or in combination with the sheath which also secures the extension graft 78 to the second delivery device 76 and holds it in a radially inwardly compressed "pre-deployment" condition.

In one example, a "self-expanding" stent expands primarily based on its own expansive force without the need for further mechanical expansion. More particularly, a stent made of a shape-memory alloy such as nitinol may allow the stent graft 4 and/or extension stent graft 78 to return to a predetermined expanded configuration upon removal of a sheath or other mechanism that maintains the stent grafts 4, 78 in its compressed, pre-deployment configuration. In another example, stents made of materials such as stainless steel may expand on their own accord once released from constraints holding them in their compressed state. Alternatively, stent grafts 4, 78, may require further manipulation, mechanical or manual expansion, such as by balloon expansion by the user. In either case, it is contemplated that stent grafts 4, 78 may expand or deploy only partially within the vessel lumen after removal of any retention mechanisms, such that additional expansion of stent grafts 4, 78 may be desired, at which time the user may implement various known and acceptable techniques to fully deploy grafts 4, 78 in the common iliac artery 48 and/or branched vessel 52. Such fully deployed stent grafts 4, 78 are illustrated in exemplary FIG. 14.

Upon deployment of the stent graft 4 with side branch 34 and deployment of extension graft 78, the pusher 10 can be removed, such as by retracting it distally from the patient through the ipsilateral iliac artery 48. As shown in FIG. 14, the extension graft 78 preferably extends from the side branch 34 of the stent graft 4 into the internal iliac artery 52. Following graft deployment and withdrawal of the delivery device 2 from the patient's body, it may be desirable to leave one or more components, such as through wire 62 in position within the descending aorta 56 to facilitate further introduction and deployment of another stent graft into the descending aorta 56, such as an AAA main body bifurcated stent graft. For example, another delivery system carrying an AAA stent graft can be tracked over the through wire 62 into the aorta and deployed therein in accordance with known systems and methods.

Thus, the pre-loaded delivery device 2 with a pusher extension 18 and a preloaded extension dilator 38 as described herein effectively and efficiently facilitates the introduction, placement and deployment of a stent graft 4 into the common iliac artery with a single through wire 62, while also facilitating the cannulation of one or more branched vessels with the extension dilator 38, including, but not limited to an internal iliac artery extending therefrom, in order to treat and/or restore patency to one or both of such vessels.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together.

The invention claimed is:

1. A prosthesis delivery device comprising:
   a pusher catheter having a proximal end, a distal end and a lumen extending there between;
   a pusher extension extending proximally from the proximal end of the pusher catheter;
   a tubular prosthesis releasably coupled to the pusher extension, wherein the tubular prosthesis comprises a main tubular body having a proximal end and a distal end and a tubular side arm extending from the main tubular body and wherein the distal end of the tubular prosthesis is adjacent to the proximal end of the pusher catheter;
   wherein the pusher extension is external to the tubular prosthesis and extends along an external surface of the tubular prosthesis;
   an extension dilator having a first end and a second end and a lumen extending between the first and second ends, wherein the extension dilator extends proximally from the proximal end of the pusher catheter, extends at least partially along the external surface of the main tubular body, into a distal end of the tubular side arm and exits a proximal end of the tubular prosthesis, and
   a delivery sheath having a proximal end, a distal end and a lumen extending there between, wherein the sheath has a first position in which the proximal end of the sheath frictionally engages the extension dilator at a location proximal to a proximal end of the prosthesis, and a second position in which the sheath is retracted to a position distal to the proximal end of the prosthesis.

2. The delivery device of claim 1 wherein the sheath retains the prosthesis in a radially-inwardly compressed delivery configuration when the sheath is in the first position.

3. The delivery device of claim 1 wherein a distal end of the tubular prosthesis is releasably coupled to the pusher extension.

4. The delivery device of claim 1 wherein a proximal end and a distal end of the tubular prosthesis are releasably coupled to the pusher extension.

5. The delivery device of claim 1 wherein the tubular prosthesis is releasably coupled to the pusher extension by at least one trigger wire.

6. The delivery device of claim 5 wherein the at least one trigger wire extends through at least a portion of the pusher catheter lumen and weaves through at least one aperture formed in the pusher extension and through at least one of a proximal end and a distal end of the prosthesis.

7. The delivery device of claim 1 wherein the prosthesis has a fenestration formed in a side wall of the main tubular body and wherein a proximal end of the tubular side arm extends from the fenestration.

8. The delivery device of claim 1 wherein the pusher extension is external to the tubular prosthesis and extends along at least a portion of the external surface of only one side of the tubular prosthesis.

9. The delivery device of claim 1 wherein the extension dilator has a first outer diameter at the first end and a second outer diameter at the second end, and wherein the second outer diameter is larger than the first outer diameter.

10. The delivery device of claim 9 wherein the first outer diameter is in a range of about 1 Fr to about 5 Fr and wherein the second outer diameter is in a range of about 8 Fr to about 14 Fr.

11. The delivery device of claim 1 wherein the extension dilator has a radially outwardly flared portion between the first and second ends.

12. The delivery device of claim 1 wherein the proximal end of the sheath tapers radially inwardly and wherein the proximal tapered end of the sheath frictionally engages the extension dilator.

13. The delivery device of claim 1 wherein a proximal segment of the extension dilator has a larger outer diameter than a distal segment of the extension dilator, and wherein the larger outer diameter segment extends proximally from the proximal end of the sheath in a delivery configuration.

14. The delivery device of claim 12 wherein the tapered proximal end of the sheath frictionally engages the extension dilator by friction fit.

15. The delivery device of claim 1 wherein the device is configured for tracking over a guide wire, the guide wire extending through the lumen of the extension dilator and through the lumen of the pusher catheter during delivery.

16. The delivery device of claim 1 wherein the pusher extension comprises at least one of a rod, a post, a wall and a support having a C-shaped cross section that corresponds to the shape of the external surface of at least a portion of the tubular prosthesis.

17. The delivery device of claim 1 wherein the pusher extension extends proximally from the proximal end of the pusher catheter to a location adjacent a proximal end of the prosthesis.

18. The delivery device of claim 1 wherein the pusher extension extends proximally from the proximal end of the pusher catheter to a location adjacent a distal end of the prosthesis.

19. A method for treating a diseased vessel comprising;
providing a prosthesis delivery device comprising a pusher catheter having a proximal end; a pusher extension extending proximally from the proximal end of the pusher catheter; a tubular prosthesis releasably coupled to the pusher extension, wherein the tubular prosthesis comprises a main tubular body having a proximal end and a distal end and a tubular side arm extending from the main tubular body and wherein the distal end of the tubular prosthesis is adjacent to the proximal end of the pusher catheter; wherein the pusher extension is external to the tubular prosthesis and extends along an external surface of the tubular prosthesis; an extension dilator having a lumen, the extension dilator extending proximally from the proximal end of the pusher catheter, extending at least partially along an external surface of the main tubular body, into a distal end of the tubular side arm and exiting a proximal end of the tubular prosthesis; a delivery sheath having a first position in which a proximal end of the sheath frictionally engages the extension dilator at a location proximal to the proximal end of the prosthesis and a second distally retracted position,
tracking the delivery device over a guide wire within a patient's vasculature to position the prosthesis in a main vessel with the tubular side arm adjacent an opening to a branch vessel, wherein the guide wire extends through the lumen of the extension dilator;
retracting the sheath to move it from the first position to the second position to expose at least the proximal end of the stent graft and the tubular side arm;
withdrawing the extension dilator from the vasculature through the proximal end of the prosthesis leaving the guide wire in place to facilitate cannulation of a branch vessel,
tracking an auxiliary sheath over the guide wire into the proximal end of the prosthesis and through the lumen of the tubular side arm until a proximal end of the auxiliary sheath is located adjacent the opening of the branch vessel to facilitate cannulation of the branch vessel;
delivering an extension prosthesis through the auxiliary sheath into the branch vessel, and
deploying the tubular prosthesis and the extension prosthesis and removing the delivery device from the patient's vasculature.

* * * * *